(12) United States Patent
Fortson et al.

(10) Patent No.: US 8,864,778 B2
(45) Date of Patent: Oct. 21, 2014

(54) APPARATUS AND METHOD FOR SUTURING BODY LUMENS

(75) Inventors: Aaron M. Fortson, Freemont, CA (US); Douglas H. Mehl, Redwood City, CA (US); Dinorah Merrill, Salida, CA (US); David J. Milazzo, Santa Clara, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 99 days.

(21) Appl. No.: 13/443,659

(22) Filed: Apr. 10, 2012

(65) Prior Publication Data

US 2013/0267967 A1    Oct. 10, 2013

(51) Int. Cl.
*A61B 17/04*    (2006.01)

(52) U.S. Cl.
USPC .......................................... 606/144; 606/139

(58) Field of Classification Search
USPC ......... 606/139, 144, 145, 146, 147, 148, 149, 606/150, 232
See application file for complete search history.

(56) References Cited

U.S. PATENT DOCUMENTS

| | | |
|---|---|---|
| 312,408 A | 2/1885 | Wackerhagen |
| 597,165 A | 1/1898 | Hall |
| 659,422 A | 10/1900 | Shidler |
| 989,231 A | 4/1911 | Davis |
| 1,574,362 A | 9/1922 | Callahan |
| 1,625,602 A | 4/1927 | Gould et al. |
| 1,940,351 A | 3/1933 | Howard |
| 2,012,776 A | 8/1935 | Roeder |
| 2,131,321 A | 10/1937 | Hart |
| 2,127,903 A | 8/1938 | Bowen |
| 2,371,978 A | 3/1945 | Perham |
| 2,397,823 A | 4/1946 | Walter |
| RE22,857 E | 3/1947 | Ogburn |
| 2,595,086 A | 11/1948 | Larzelere |
| 2,588,589 A | 3/1952 | Tauber |

(Continued)

FOREIGN PATENT DOCUMENTS

| | | |
|---|---|---|
| DE | 912619 | 5/1954 |
| DE | 4210724 | 7/1993 |

(Continued)

OTHER PUBLICATIONS

U.S. Appl. No. 10/948,445, filed Sep. 22, 2004, McIntosh.

(Continued)

*Primary Examiner* — Julian W Woo
*Assistant Examiner* — Lucas Paez
(74) *Attorney, Agent, or Firm* — Workman Nydegger; Randy Shen

(57) ABSTRACT

An apparatus for suturing body lumens is provided. The apparatus includes a flexible elongated member that has a proximal end, a distal end, a central passage and multiple needle lumens extending from the proximal end toward the distal end. The flexible elongated member further includes an elongated subsection spanning from the end of the needle lumens in the elongated member to a barrel portion that includes corresponding needle lumens on the proximal end of the elongated member. The elongated subsection provides sufficient space between the needles and the barrel portion to allow transapical insertion of the elongated member into a body lumen. The apparatus further includes needles disposed within and advanceable from the needle lumens. The apparatus also includes a handle disposed at the proximal end of the elongated member. The handle is operable to retract the needles through the needle lumens toward the handle at the proximal end.

18 Claims, 6 Drawing Sheets

(56) References Cited

U.S. PATENT DOCUMENTS

| | | |
|---|---|---|
| 2,646,045 A | 7/1953 | Priestley |
| 2,692,599 A | 10/1954 | Creelman |
| 2,941,489 A | 6/1960 | Fischbein |
| 2,959,172 A | 11/1960 | Held |
| 3,033,156 A | 5/1962 | Verlish |
| 3,104,666 A | 9/1963 | Hale et al. |
| 3,197,102 A | 7/1965 | Bates et al. |
| 3,359,983 A | 12/1967 | Northey |
| 3,413,397 A | 11/1968 | Bierbaum et al. |
| 3,422,181 A | 1/1969 | Chirgwin, Jr. |
| 3,470,875 A | 10/1969 | Johnson |
| 3,485,234 A | 12/1969 | Stevens |
| 3,587,115 A | 6/1971 | Shiley |
| 3,630,205 A | 12/1971 | Listner |
| 3,653,388 A | 4/1972 | Tenckhoff |
| 3,665,926 A | 5/1972 | Flores |
| 3,776,237 A | 12/1973 | Hill et al. |
| 3,802,438 A | 4/1974 | Wolvek |
| 3,820,544 A | 6/1974 | Semm |
| 3,840,017 A | 10/1974 | Violante |
| 3,874,388 A | 4/1975 | King et al. |
| 3,878,848 A | 4/1975 | Hiebert |
| 3,918,455 A | 11/1975 | Coplan |
| 3,926,194 A | 12/1975 | Greenberg et al. |
| 3,939,820 A | 2/1976 | Grayzel |
| 3,985,138 A | 10/1976 | Jarvik |
| 4,018,228 A | 4/1977 | Goosen |
| 4,069,825 A | 1/1978 | Akiyama |
| 4,109,658 A | 8/1978 | Hughes |
| 4,128,100 A | 12/1978 | Wendorff |
| 4,135,623 A | 1/1979 | Thyen |
| 4,161,951 A | 7/1979 | Scanlan, Jr. |
| 4,168,073 A | 9/1979 | LaRue |
| 4,182,339 A | 1/1980 | Hardy, Jr. |
| 4,185,636 A | 1/1980 | Gabbay et al. |
| 4,216,776 A | 8/1980 | Downie et al. |
| 4,217,665 A | 8/1980 | Bex et al. |
| 4,235,177 A | 11/1980 | Arbuckle |
| 4,235,238 A | 11/1980 | Ogiu et al. |
| 4,316,469 A | 2/1982 | Kapitanov |
| 4,317,445 A | 3/1982 | Robinson |
| 4,411,654 A | 10/1983 | Boarini et al. |
| 4,412,832 A | 11/1983 | Kling et al. |
| 4,437,465 A | 3/1984 | Nomoto et al. |
| 4,469,101 A | 9/1984 | Coleman et al. |
| 4,492,229 A | 1/1985 | Grunwald |
| 4,493,323 A | 1/1985 | Albright et al. |
| 4,553,543 A | 11/1985 | Amarasinghe |
| 4,586,614 A | 5/1986 | Ger |
| 4,587,969 A | 5/1986 | Gillis |
| 4,596,559 A | 6/1986 | Fleishhacker |
| 4,610,248 A | 9/1986 | Rosenberg |
| 4,629,450 A | 12/1986 | Suzuki et al. |
| 4,651,733 A | 3/1987 | Mobin-Uddin |
| 4,655,211 A | 4/1987 | Sakamoto et al. |
| 4,702,250 A | 10/1987 | Orvil et al. |
| 4,723,549 A | 2/1988 | Wholey et al. |
| 4,738,666 A | 4/1988 | Fuqua |
| 4,744,364 A | 5/1988 | Kensey |
| 4,748,982 A | 6/1988 | Horzewski et al. |
| 4,782,954 A | 11/1988 | Reynolds |
| 4,803,984 A | 2/1989 | Narayanan et al. |
| 4,823,794 A * | 4/1989 | Pierce ............................ 606/232 |
| 4,836,205 A | 6/1989 | Barrett |
| 4,845,851 A | 7/1989 | Warthen |
| 4,848,341 A | 7/1989 | Ahmad |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,917,089 A | 4/1990 | Sideris |
| 4,926,860 A | 5/1990 | Stice et al. |
| 4,929,246 A | 5/1990 | Sinofsky |
| 4,935,027 A | 6/1990 | Yoon |
| 4,950,285 A | 8/1990 | Wilk |
| 4,957,498 A | 9/1990 | Caspari et al. |
| 4,966,600 A | 10/1990 | Songer et al. |
| 4,981,149 A | 1/1991 | Yoon et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich et al. |
| 5,021,059 A | 6/1991 | Kensey et al. |
| 5,037,433 A | 8/1991 | Wilk et al. |
| 5,041,129 A | 8/1991 | Hayhurst et al. |
| 5,047,039 A | 9/1991 | Avant et al. |
| 5,059,201 A | 10/1991 | Asnis |
| 5,061,274 A | 10/1991 | Kensey |
| 5,074,874 A | 12/1991 | Yoon et al. |
| 5,078,721 A | 1/1992 | McKeating |
| 5,080,664 A | 1/1992 | Jain |
| 5,100,419 A | 3/1992 | Ehlers |
| 5,100,422 A | 3/1992 | Berguer et al. |
| 5,100,432 A | 3/1992 | Matsutani |
| 5,108,421 A | 4/1992 | Fowler |
| 5,109,780 A | 5/1992 | Slouf et al. |
| 5,129,882 A | 7/1992 | Weldon et al. |
| 5,129,912 A | 7/1992 | Noda et al. |
| 5,129,913 A | 7/1992 | Ruppert |
| 5,144,961 A | 9/1992 | Chen et al. |
| 5,147,373 A | 9/1992 | Ferzli |
| 5,156,788 A | 10/1992 | Chesterfield et al. |
| 5,160,339 A | 11/1992 | Chen et al. |
| 5,163,946 A | 11/1992 | Li |
| 5,169,041 A | 12/1992 | Tan |
| 5,171,251 A | 12/1992 | Bregen et al. |
| 5,176,691 A | 1/1993 | Pierce |
| 5,178,629 A | 1/1993 | Kammerer |
| 5,192,294 A | 3/1993 | Blake, III |
| 5,192,301 A | 3/1993 | Kamiya et al. |
| 5,192,302 A | 3/1993 | Kensey et al. |
| 5,201,744 A | 4/1993 | Jones |
| 5,207,703 A | 5/1993 | Jain |
| 5,211,650 A | 5/1993 | Noda |
| 5,217,470 A | 6/1993 | Weston |
| 5,217,485 A | 6/1993 | Liv et al. |
| 5,219,358 A | 6/1993 | Bendel et al. |
| 5,222,974 A | 6/1993 | Kensey et al. |
| 5,234,443 A | 8/1993 | Phan et al. |
| 5,234,445 A | 8/1993 | Walker et al. |
| 5,237,985 A | 8/1993 | Hodgson et al. |
| 5,242,427 A | 9/1993 | Bilweis |
| 5,250,033 A | 10/1993 | Evans et al. |
| 5,250,053 A | 10/1993 | Snyder |
| 5,250,054 A | 10/1993 | Li |
| 5,254,105 A | 10/1993 | Haaga |
| 5,254,113 A | 10/1993 | Wilk |
| 5,254,126 A | 10/1993 | Filipi et al. |
| 5,258,003 A | 11/1993 | Ciaglia et al. |
| 5,259,846 A | 11/1993 | Granger et al. |
| 5,275,616 A | 1/1994 | Fowler |
| 5,279,311 A | 1/1994 | Snyder |
| 5,281,236 A | 1/1994 | Bognato et al. |
| 5,281,237 A | 1/1994 | Gimpelson |
| 5,284,485 A | 2/1994 | Kammerer et al. |
| 5,285,945 A | 2/1994 | Brinkerhoff et al. |
| 5,289,963 A | 3/1994 | McGarry et al. |
| 5,290,284 A | 3/1994 | Adair |
| 5,290,297 A | 3/1994 | Phillips |
| 5,290,310 A | 3/1994 | Makower et al. |
| 5,292,309 A | 3/1994 | VanTassel et al. |
| 5,292,327 A | 3/1994 | Dodd et al. |
| 5,292,332 A | 3/1994 | Lee |
| 5,293,881 A | 3/1994 | Green et al. |
| 5,295,993 A | 3/1994 | Green |
| 5,300,085 A | 4/1994 | Yock |
| 5,304,184 A | 4/1994 | Hathaway et al. |
| 5,304,185 A | 4/1994 | Taylor |
| 5,306,254 A | 4/1994 | Nash et al. |
| 5,312,024 A | 5/1994 | Grant et al. |
| 5,312,423 A | 5/1994 | Rosenbluth et al. |
| 5,318,578 A | 6/1994 | Hasson |
| 5,320,629 A | 6/1994 | Noda et al. |
| 5,320,632 A | 6/1994 | Heidmueller |

(56) References Cited

U.S. PATENT DOCUMENTS

| | | |
|---|---|---|
| 5,330,445 A | 7/1994 | Haaga |
| 5,330,491 A | 7/1994 | Walker et al. |
| 5,334,217 A | 8/1994 | Das |
| 5,336,229 A | 8/1994 | Noda |
| 5,336,230 A | 8/1994 | Leichtling et al. |
| 5,336,231 A | 8/1994 | Adair |
| 5,342,369 A | 8/1994 | Harryman, II |
| 5,353,974 A | 10/1994 | Maurizio |
| 5,354,312 A | 10/1994 | Brinkerhoff et al. |
| 5,364,407 A | 11/1994 | Poll |
| 5,364,408 A | 11/1994 | Gordon |
| 5,368,595 A | 11/1994 | Lewis |
| 5,368,601 A | 11/1994 | Sauer et al. |
| 5,374,275 A | 12/1994 | Bradley et al. |
| 5,374,278 A | 12/1994 | Chesterfield et al. |
| 5,376,096 A | 12/1994 | Foster |
| 5,383,896 A | 1/1995 | Gershony et al. |
| 5,383,905 A | 1/1995 | Golds et al. |
| 5,385,569 A | 1/1995 | Swor |
| 5,387,221 A | 2/1995 | Bisgaard |
| 5,387,227 A | 2/1995 | Grice |
| 5,391,176 A | 2/1995 | de la Torre |
| 5,391,182 A | 2/1995 | Chin |
| 5,395,332 A | 3/1995 | Ressemann et al. |
| 5,395,349 A | 3/1995 | Quiachon et al. |
| 5,397,310 A | 3/1995 | Chu et al. |
| 5,397,325 A | 3/1995 | Delia Badia et al. |
| 5,397,326 A | 3/1995 | Mangum |
| 5,403,329 A | 4/1995 | Hinchcliffe |
| 5,403,331 A | 4/1995 | Chesterfield et al. |
| 5,403,338 A | 4/1995 | Milo |
| 5,405,352 A | 4/1995 | Weston |
| 5,411,481 A | 5/1995 | Allen et al. |
| 5,413,571 A | 5/1995 | Katsaros et al. |
| 5,417,684 A | 5/1995 | Jackson et al. |
| 5,417,699 A | 5/1995 | Klein et al. |
| 5,419,765 A | 5/1995 | Weldon et al. |
| 5,425,705 A | 6/1995 | Evard et al. |
| 5,425,737 A | 6/1995 | Burbank et al. |
| 5,425,740 A | 6/1995 | Hutchinson, Jr. |
| 5,431,666 A | 7/1995 | Sauer et al. |
| 5,433,700 A | 7/1995 | Peters |
| 5,452,733 A | 9/1995 | Sterman et al. |
| 5,454,822 A | 10/1995 | Schob et al. |
| 5,454,834 A | 10/1995 | Boebel et al. |
| 5,458,574 A | 10/1995 | Machold et al. |
| 5,462,560 A | 10/1995 | Stevens |
| 5,462,561 A | 10/1995 | Voda |
| 5,464,426 A | 11/1995 | Bonutti |
| 5,466,241 A | 11/1995 | Leroy et al. |
| 5,470,338 A | 11/1995 | Whitfield et al. |
| 5,474,568 A | 12/1995 | Scott |
| 5,476,469 A | 12/1995 | Hathaway et al. |
| 5,476,470 A | 12/1995 | Fitzgibbons, Jr. |
| 5,478,309 A | 12/1995 | Sweezer et al. |
| 5,478,353 A | 12/1995 | Yoon |
| 5,480,407 A | 1/1996 | Wan et al. |
| 5,486,190 A | 1/1996 | Green |
| 5,489,295 A | 2/1996 | Piplani et al. |
| 5,496,332 A | 3/1996 | Sierra et al. |
| 5,507,744 A | 4/1996 | Tay et al. |
| 5,507,755 A | 4/1996 | Gresl et al. |
| 5,507,757 A | 4/1996 | Sauer et al. |
| 5,507,758 A | 4/1996 | Thomason et al. |
| 5,509,902 A | 4/1996 | Raulerson |
| 5,520,655 A | 5/1996 | Davila et al. |
| 5,520,665 A | 5/1996 | Fleetwood |
| 5,520,691 A | 5/1996 | Branch |
| 5,520,702 A | 5/1996 | Sauer et al. |
| 5,527,321 A | 6/1996 | Hinchcliffe |
| 5,527,322 A | 6/1996 | Klein et al. |
| D372,310 S | 7/1996 | Hartnett |
| 5,531,700 A | 7/1996 | Moore et al. |
| 5,536,273 A | 7/1996 | Lehrer |
| 5,540,701 A | 7/1996 | Sharkey et al. |
| 5,540,703 A | 7/1996 | Barker, Jr. et al. |
| 5,540,704 A | 7/1996 | Gordon et al. |
| 5,545,171 A | 8/1996 | Sharkey et al. |
| 5,545,178 A | 8/1996 | Kensey et al. |
| 5,545,180 A | 8/1996 | Le et al. |
| 5,549,618 A | 8/1996 | Fleenor et al. |
| 5,549,631 A | 8/1996 | Bonutti |
| 5,554,162 A | 9/1996 | DeLange |
| 5,562,684 A | 10/1996 | Kammerer |
| 5,562,686 A | 10/1996 | Sauer et al. |
| 5,562,688 A | 10/1996 | Riza |
| 5,562,728 A | 10/1996 | Lazarus et al. |
| 5,567,435 A | 10/1996 | Hubbell et al. |
| 5,569,269 A | 10/1996 | Hart et al. |
| 5,569,271 A | 10/1996 | Hoel |
| 5,571,120 A | 11/1996 | Yoon |
| 5,573,540 A | 11/1996 | Yoon |
| 5,584,842 A | 12/1996 | Fogarty et al. |
| 5,591,177 A | 1/1997 | Lehrer |
| 5,591,179 A | 1/1997 | Edelstein |
| 5,591,206 A | 1/1997 | Moufarrege |
| 5,593,421 A | 1/1997 | Bauer |
| 5,601,572 A | 2/1997 | Middleman et al. |
| 5,603,718 A | 2/1997 | Xu |
| 5,607,435 A | 3/1997 | Sachdeva et al. |
| 5,609,597 A | 3/1997 | Lehrer |
| 5,611,794 A | 3/1997 | Sauer et al. |
| 5,613,974 A | 3/1997 | Andreas et al. |
| 5,613,975 A | 3/1997 | Christy |
| 5,624,446 A | 4/1997 | Harryman, II |
| 5,626,588 A | 5/1997 | Sauer et al. |
| 5,643,289 A | 7/1997 | Sauer et al. |
| 5,643,295 A | 7/1997 | Yoon |
| 5,643,318 A | 7/1997 | Tsukernik et al. |
| 5,649,959 A | 7/1997 | Hannam et al. |
| 5,662,664 A | 9/1997 | Gordon et al. |
| 5,669,917 A | 9/1997 | Sauer et al. |
| 5,676,689 A | 10/1997 | Kensey et al. |
| 5,700,273 A | 12/1997 | Buelna et al. |
| 5,707,379 A | 1/1998 | Fleenor et al. |
| 5,713,910 A | 2/1998 | Gordon et al. |
| 5,716,369 A | 2/1998 | Riza |
| 5,720,574 A | 2/1998 | Barella |
| 5,720,757 A | 2/1998 | Hathaway et al. |
| 5,722,981 A | 3/1998 | Stevens |
| 5,725,552 A | 3/1998 | Kotula et al. |
| 5,728,109 A | 3/1998 | Schulze et al. |
| 5,728,114 A | 3/1998 | Evans et al. |
| 5,728,133 A | 3/1998 | Kontos |
| 5,728,151 A | 3/1998 | Garrison et al. |
| 5,741,276 A | 4/1998 | Poloyko et al. |
| 5,741,280 A | 4/1998 | Fleenor |
| 5,746,755 A | 5/1998 | Wood et al. |
| 5,749,890 A | 5/1998 | Shaknovich |
| 5,755,727 A | 5/1998 | Kontos |
| 5,759,188 A | 6/1998 | Yoon |
| 5,766,183 A | 6/1998 | Sauer |
| 5,766,186 A | 6/1998 | Faraz et al. |
| 5,766,217 A | 6/1998 | Christy |
| 5,769,862 A | 6/1998 | Kammerer et al. |
| 5,779,719 A | 7/1998 | Klein et al. |
| 5,782,860 A | 7/1998 | Epstein et al. |
| 5,782,861 A | 7/1998 | Cragg et al. |
| 5,792,151 A | 8/1998 | Heck et al. |
| 5,792,152 A | 8/1998 | Klein et al. |
| 5,797,928 A | 8/1998 | Kogasaka |
| 5,797,929 A | 8/1998 | Andreas et al. |
| 5,799,661 A | 9/1998 | Boyd et al. |
| 5,810,849 A | 9/1998 | Kontos |
| 5,810,850 A | 9/1998 | Hathaway et al. |
| 5,814,069 A | 9/1998 | Schulze et al. |
| 5,817,113 A | 10/1998 | Gifford, III et al. |
| 5,820,631 A | 10/1998 | Nobles |
| 5,824,010 A | 10/1998 | McDonald |
| 5,824,111 A | 10/1998 | Schall et al. |
| 5,830,125 A | 11/1998 | Scribner et al. |
| 5,836,955 A | 11/1998 | Buelna et al. |
| 5,836,956 A | 11/1998 | Buelna et al. |
| 5,846,253 A | 12/1998 | Buelna et al. |

(56) References Cited

U.S. PATENT DOCUMENTS

| | | |
|---|---|---|
| 5,848,714 A | 12/1998 | Robson et al. |
| 5,855,585 A | 1/1999 | Kontos |
| 5,860,963 A | 1/1999 | Azam et al. |
| 5,860,990 A | 1/1999 | Nobles et al. |
| 5,860,991 A | 1/1999 | Klein et al. |
| 5,861,005 A | 1/1999 | Kontos |
| 5,871,490 A | 2/1999 | Schulze et al. |
| 5,871,502 A | 2/1999 | Suryadevara |
| 5,873,876 A | 2/1999 | Christy |
| 5,876,411 A | 3/1999 | Kontos |
| 5,897,487 A | 4/1999 | Ouchi |
| 5,897,564 A | 4/1999 | Schulze et al. |
| 5,902,311 A | 5/1999 | Andreas et al. |
| 5,904,597 A | 5/1999 | Doi et al. |
| 5,904,690 A | 5/1999 | Middleman et al. |
| 5,904,697 A | 5/1999 | Gifford, III et al. |
| 5,906,631 A | 5/1999 | Imran |
| 5,919,207 A | 7/1999 | Taheri |
| 5,921,994 A | 7/1999 | Andreas et al. |
| 5,928,266 A | 7/1999 | Kontos |
| 5,951,590 A | 9/1999 | Goldfarb |
| 5,954,732 A | 9/1999 | Hart et al. |
| 5,957,936 A | 9/1999 | Yoon et al. |
| 5,957,937 A | 9/1999 | Yoon |
| 5,957,938 A | 9/1999 | Zhu et al. |
| 5,964,773 A | 10/1999 | Greenstein |
| 5,964,782 A | 10/1999 | Lafontaine et al. |
| 5,972,030 A | 10/1999 | Garrison et al. |
| 5,976,161 A | 11/1999 | Kirsch et al. |
| 5,980,539 A | 11/1999 | Kontos |
| 5,997,555 A | 12/1999 | Kontos |
| 6,001,109 A | 12/1999 | Kontos |
| 6,022,372 A | 2/2000 | Kontos |
| 6,024,747 A | 2/2000 | Kontos |
| 6,036,699 A * | 3/2000 | Andreas et al. ............... 606/139 |
| 6,042,601 A | 3/2000 | Smith |
| 6,048,351 A | 4/2000 | Gordon et al. |
| 6,048,354 A | 4/2000 | Lawrence |
| 6,048,357 A | 4/2000 | Kontos |
| 6,059,800 A * | 5/2000 | Hart et al. ............... 606/144 |
| 6,068,603 A | 5/2000 | Suzuki |
| 6,077,276 A | 6/2000 | Kontos |
| 6,077,279 A | 6/2000 | Kontos |
| 6,117,144 A | 9/2000 | Nobles et al. |
| 6,117,145 A | 9/2000 | Wood et al. |
| 6,126,675 A | 10/2000 | Shchervinsky et al. |
| 6,132,439 A | 10/2000 | Kontos |
| 6,132,440 A | 10/2000 | Hathaway et al. |
| 6,136,010 A | 10/2000 | Modesitt et al. |
| 6,139,556 A | 10/2000 | Kontos |
| 6,152,936 A | 11/2000 | Christy et al. |
| 6,165,183 A | 12/2000 | Kuehn et al. |
| 6,165,204 A | 12/2000 | Levinson et al. |
| 6,190,396 B1 | 2/2001 | Whitin et al. |
| 6,197,042 B1 | 3/2001 | Ginn et al. |
| 6,206,893 B1 | 3/2001 | Klein et al. |
| 6,206,895 B1 | 3/2001 | Levinson |
| 6,245,079 B1 | 6/2001 | Nobles et al. |
| 6,248,124 B1 | 6/2001 | Pedros et al. |
| 6,296,657 B1 | 10/2001 | Brucker |
| 6,302,870 B1 | 10/2001 | Jacobsen et al. |
| 6,348,059 B1 | 2/2002 | Hathaway et al. |
| 6,355,050 B1 * | 3/2002 | Andreas et al. ............... 606/144 |
| 6,358,258 B1 | 3/2002 | Arcia et al. |
| 6,395,015 B1 | 5/2002 | Borst et al. |
| 6,428,472 B1 | 8/2002 | Haas |
| 6,428,549 B1 | 8/2002 | Kontos |
| 6,436,109 B1 | 8/2002 | Kontos |
| 6,443,963 B1 | 9/2002 | Baldwin et al. |
| 6,451,031 B1 | 9/2002 | Kontos |
| 6,511,489 B2 | 1/2003 | Field et al. |
| 6,517,553 B2 | 2/2003 | Klein et al. |
| 6,533,812 B2 | 3/2003 | Swanson et al. |
| 6,551,330 B1 | 4/2003 | Bain et al. |
| 6,558,399 B1 | 5/2003 | Isbell et al. |
| 6,562,052 B2 | 5/2003 | Nobles et al. |
| 6,569,185 B2 | 5/2003 | Ungs |
| 6,572,629 B2 | 6/2003 | Kalloo et al. |
| 6,610,072 B1 | 8/2003 | Christy et al. |
| 6,623,509 B2 | 9/2003 | Ginn |
| 6,623,510 B2 | 9/2003 | Carly et al. |
| 6,632,237 B2 | 10/2003 | Ben-David et al. |
| 6,641,592 B1 | 11/2003 | Sauer et al. |
| 6,663,655 B2 | 12/2003 | Ginn et al. |
| 6,676,685 B2 | 1/2004 | Pedros et al. |
| 6,695,867 B2 | 2/2004 | Ginn et al. |
| 6,716,228 B2 | 4/2004 | Tal |
| 6,743,195 B2 | 6/2004 | Zucker |
| 6,743,259 B2 | 6/2004 | Ginn |
| 6,749,621 B2 | 6/2004 | Pantages et al. |
| 6,749,622 B2 | 6/2004 | McGuckin, Jr. et al. |
| 6,837,906 B2 | 1/2005 | Ginn |
| 6,846,319 B2 | 1/2005 | Ginn et al. |
| 6,890,343 B2 | 5/2005 | Ginn et al. |
| 6,896,692 B2 | 5/2005 | Ginn et al. |
| 6,911,034 B2 | 6/2005 | Nobles et al. |
| 6,939,357 B2 | 9/2005 | Navarro et al. |
| 6,964,668 B2 | 11/2005 | Modesitt et al. |
| 6,969,371 B2 | 11/2005 | Palasis et al. |
| 6,969,397 B2 | 11/2005 | Ginn |
| 7,001,400 B1 | 2/2006 | Modesitt et al. |
| 7,029,480 B2 | 4/2006 | Klein et al. |
| 7,029,481 B1 | 4/2006 | Burdulis, Jr. et al. |
| 7,048,747 B2 | 5/2006 | Arcia et al. |
| 7,063,710 B2 | 6/2006 | Takamoto et al. |
| 7,083,635 B2 | 8/2006 | Ginn |
| 7,108,710 B2 | 9/2006 | Anderson |
| 7,112,225 B2 | 9/2006 | Ginn |
| 7,160,309 B2 | 1/2007 | Voss |
| 7,179,266 B2 | 2/2007 | Kontos |
| 7,229,458 B2 | 6/2007 | Boecker et al. |
| 7,235,087 B2 | 6/2007 | Modesitt et al. |
| 7,316,704 B2 | 1/2008 | Bagaoisan et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| 7,361,183 B2 | 4/2008 | Ginn |
| 7,361,185 B2 | 4/2008 | O'Malley et al. |
| 7,377,927 B2 | 5/2008 | Burdulis, Jr. et al. |
| 7,390,328 B2 | 6/2008 | Modesitt |
| 7,393,363 B2 | 7/2008 | Ginn |
| 7,442,198 B2 | 10/2008 | Gellman et al. |
| 7,445,626 B2 | 11/2008 | Songer et al. |
| 7,449,024 B2 | 11/2008 | Stafford |
| 7,462,188 B2 | 12/2008 | McIntosh |
| 7,753,923 B2 | 7/2010 | St. Goar et al. |
| 7,837,696 B2 | 11/2010 | Modesitt et al. |
| 7,842,047 B2 | 11/2010 | Modesitt et al. |
| 7,842,048 B2 | 11/2010 | Ma |
| 7,842,049 B2 | 11/2010 | Voss |
| 7,846,170 B2 | 12/2010 | Modesitt et al. |
| 7,850,701 B2 | 12/2010 | Modesitt |
| 7,883,517 B2 | 2/2011 | Pantages et al. |
| 8,038,688 B2 | 10/2011 | Modesitt et al. |
| 8,048,092 B2 | 11/2011 | Modesitt et al. |
| 8,057,491 B2 | 11/2011 | Modesitt et al. |
| 8,083,754 B2 | 12/2011 | Pantages et al. |
| 8,137,364 B2 | 3/2012 | Zung et al. |
| 8,172,860 B2 | 5/2012 | Zung et al. |
| 8,202,281 B2 | 6/2012 | Voss |
| 8,211,122 B2 | 7/2012 | McIntosh |
| 8,252,008 B2 | 8/2012 | Ma |
| 8,257,368 B2 | 9/2012 | McIntosh |
| 8,267,947 B2 | 9/2012 | Pantages et al. |
| 2001/0046518 A1 | 11/2001 | Sawhney |
| 2002/0045908 A1 | 4/2002 | Nobles et al. |
| 2002/0095164 A1 | 7/2002 | Andreas et al. |
| 2002/0099389 A1 | 7/2002 | Michler et al. |
| 2002/0106409 A1 | 8/2002 | Sawhney et al. |
| 2002/0177876 A1 | 11/2002 | Roby et al. |
| 2003/0093093 A1 | 5/2003 | Modesitt et al. |
| 2003/0171764 A1 | 9/2003 | Debbas |
| 2003/0195529 A1 | 10/2003 | Takamoto et al. |
| 2004/0009205 A1 | 1/2004 | Sawhney |

(56) References Cited

U.S. PATENT DOCUMENTS

| | | | |
|---|---|---|---|
| 2004/0092964 A1 | 5/2004 | Modesitt et al. | |
| 2004/0093027 A1 | 5/2004 | Fabisiak et al. | |
| 2004/0097978 A1 | 5/2004 | Modesitt et al. | |
| 2004/0127940 A1 | 7/2004 | Ginn et al. | |
| 2004/0143290 A1 | 7/2004 | Brightbill | |
| 2004/0158127 A1 | 8/2004 | Okada | |
| 2004/0158287 A1 | 8/2004 | Cragg et al. | |
| 2004/0167511 A1 | 8/2004 | Buehlmann et al. | |
| 2004/0181238 A1 | 9/2004 | Zarbatany et al. | |
| 2004/0186487 A1 | 9/2004 | Klein et al. | |
| 2004/0191277 A1 | 9/2004 | Sawhney et al. | |
| 2004/0215232 A1 | 10/2004 | Belhe et al. | |
| 2004/0225301 A1 | 11/2004 | Roop et al. | |
| 2004/0267193 A1 | 12/2004 | Bagaoisan et al. | |
| 2004/0267308 A1 | 12/2004 | Bagaoisan et al. | |
| 2005/0070923 A1 | 3/2005 | McIntosh | |
| 2005/0075665 A1 | 4/2005 | Brenzel et al. | |
| 2005/0085851 A1 | 4/2005 | Fiehler et al. | |
| 2005/0085854 A1 | 4/2005 | Ginn | |
| 2005/0085855 A1 | 4/2005 | Forsberg | |
| 2005/0121042 A1 | 6/2005 | Belhe et al. | |
| 2005/0149117 A1 | 7/2005 | Khosravi et al. | |
| 2005/0177189 A1 | 8/2005 | Ginn et al. | |
| 2005/0222614 A1 | 10/2005 | Ginn et al. | |
| 2005/0245876 A1 | 11/2005 | Khosravi et al. | |
| 2005/0267528 A1 | 12/2005 | Ginn et al. | |
| 2005/0273137 A1 | 12/2005 | Ginn | |
| 2006/0034930 A1 | 2/2006 | Khosravi et al. | |
| 2006/0047313 A1 | 3/2006 | Khanna et al. | |
| 2006/0069397 A1* | 3/2006 | Nobles et al. | 606/144 |
| 2006/0100664 A1 | 5/2006 | Pai et al. | |
| 2006/0167477 A1 | 7/2006 | Arcia et al. | |
| 2006/0173469 A1 | 8/2006 | Klein | |
| 2006/0253037 A1 | 11/2006 | Ginn et al. | |
| 2006/0253072 A1 | 11/2006 | Pai et al. | |
| 2007/0005079 A1 | 1/2007 | Zarbatany et al. | |
| 2007/0032801 A1 | 2/2007 | Pantages et al. | |
| 2007/0060950 A1 | 3/2007 | Khosravi et al. | |
| 2007/0123817 A1 | 5/2007 | Khosravi et al. | |
| 2007/0282354 A1 | 12/2007 | McIntosh | |
| 2008/0009794 A1 | 1/2008 | Bagaoisan et al. | |
| 2008/0065151 A1 | 3/2008 | Ginn | |
| 2008/0065152 A1 | 3/2008 | Carley | |
| 2008/0287967 A1 | 11/2008 | Andreas et al. | |
| 2008/0319458 A1 | 12/2008 | Reynolds | |
| 2009/0036906 A1 | 2/2009 | Stafford | |
| 2009/0048615 A1 | 2/2009 | McIntosh | |
| 2009/0088779 A1 | 4/2009 | Zung et al. | |
| 2011/0066184 A1 | 3/2011 | Modesitt et al. | |
| 2011/0071567 A1 | 3/2011 | Modesitt et al. | |
| 2011/0077670 A1* | 3/2011 | Modesitt et al. | 606/144 |
| 2011/0196387 A1 | 8/2011 | Pantages et al. | |
| 2012/0016383 A1* | 1/2012 | Sauer et al. | 606/144 |
| 2012/0053600 A1 | 3/2012 | Fortson | |
| 2012/0150201 A1 | 6/2012 | Pantages et al. | |
| 2012/0283749 A1* | 11/2012 | Sauer | 606/144 |
| 2012/0316579 A1 | 12/2012 | Ma | |
| 2013/0006277 A1 | 1/2013 | Stafford | |
| 2013/0012962 A1 | 1/2013 | Stone | |
| 2013/0066340 A1 | 3/2013 | Pantages et al. | |
| 2013/0190781 A1 | 7/2013 | Fortson et al. | |

FOREIGN PATENT DOCUMENTS

| | | |
|---|---|---|
| DE | 9217932 | 7/1993 |
| DE | 4220283 | 12/1993 |
| DE | 10211360 | 10/2003 |
| EP | 0 140 557 | 5/1985 |
| EP | 0 207 545 | 1/1987 |
| EP | 0 474 887 | 3/1992 |
| EP | 0 478 358 | 4/1992 |
| EP | 0 478 887 | 4/1992 |
| EP | 0 542 126 | 5/1993 |
| EP | 0 568 098 | 11/1993 |
| EP | 0 589 409 | 3/1994 |
| EP | 0 624 343 | 11/1994 |
| EP | 0 669 101 | 8/1995 |
| EP | 0 669 102 | 8/1995 |
| EP | 0 669 103 | 8/1995 |
| EP | 0 684 012 | 11/1995 |
| EP | 0 812 571 | 12/1997 |
| EP | 0 941 698 | 9/1999 |
| FR | 1059544 | 3/1954 |
| FR | 2768324 | 3/1999 |
| JP | 51143386 | 11/1976 |
| JP | 5220794 | 2/1977 |
| JP | 2119866 | 5/1990 |
| JP | 542161 | 2/1993 |
| SU | 820810 | 4/1981 |
| SU | 993922 | 2/1983 |
| SU | 1093329 | 5/1984 |
| SU | 1174036 | 8/1985 |
| SU | 1544383 | 2/1990 |
| SU | 1648400 | 5/1991 |
| WO | WO 85/03858 | 9/1985 |
| WO | WO 01/35833 | 2/1994 |
| WO | WO 94/05213 | 3/1994 |
| WO | WO 94/13211 | 6/1994 |
| WO | WO 94/27503 | 12/1994 |
| WO | WO 94/28801 | 12/1994 |
| WO | WO 95/05121 | 2/1995 |
| WO | WO 95/13021 | 5/1995 |
| WO | WO 95/25468 | 9/1995 |
| WO | WO 95/35065 | 12/1995 |
| WO | WO 96/09006 | 3/1996 |
| WO | WO 97/00046 | 1/1997 |
| WO | WO 97/03613 | 2/1997 |
| WO | WO 97/07745 | 3/1997 |
| WO | WO 97/10764 | 3/1997 |
| WO | WO 97/13461 | 4/1997 |
| WO | WO 97/17901 | 5/1997 |
| WO | WO 97/20505 | 6/1997 |
| WO | WO 97/27897 | 8/1997 |
| WO | WO 98/04195 | 2/1998 |
| WO | WO 98/42262 | 10/1998 |
| WO | WO 99/47049 | 9/1999 |
| WO | WO 00/12013 | 3/2000 |
| WO | WO 00/51498 | 9/2000 |
| WO | WO 00/69342 | 11/2000 |
| WO | WO 01/19259 | 3/2001 |
| WO | WO 02/36021 | 5/2002 |
| WO | WO 02/062234 | 8/2002 |
| WO | WO 03/003925 | 1/2003 |
| WO | WO 03/094748 | 11/2003 |
| WO | WO 03/099134 | 12/2003 |
| WO | WO 2005/000126 | 1/2005 |
| WO | WO 2005/023119 | 3/2005 |
| WO | WO 2005/025430 | 3/2005 |
| WO | WO 2005/030060 | 4/2005 |
| WO | WO 2005/041782 | 5/2005 |
| WO | WO 2005/063129 | 7/2005 |
| WO | WO 2005/065549 | 7/2005 |
| WO | WO 2005/092204 | 10/2005 |
| WO | WO 2005/112782 | 12/2005 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/115901 | 11/2006 |
| WO | WO 2006/115904 | 11/2006 |
| WO | WO 2006/118877 | 11/2006 |
| WO | WO 2007/019016 | 2/2007 |
| WO | WO 2007/081836 | 7/2007 |

OTHER PUBLICATIONS

U.S. Appl. No. 13/445,053, filed Apr. 24, 2012, Fortson et al.
U.S. Appl. No. 13/525,875, filed Jun. 18, 2012, Voss.
U.S. Appl. No. 60/506,536, filed Sep. 26, 2003, McIntosh.
U.S. Appl. No. 60/540,811, filed Jan. 30, 2004, McIntosh.
U.S. Appl. No. 60/946,063, filed Jun. 25, 2007, Reynolds.
U.S. Appl. No. 90/006,469, filed Nov. 29, 2002, Modesitt, et al.
US 5,820,544, 06/1974, Semm (withdrawn).

(56) References Cited

OTHER PUBLICATIONS

Cardiac Catheterization and Angiography, 3rd Ed., Lea & Febiger, Philadelphia, pp. 1-49, 52-247. 1986.
Cardio-Thoracic Systems Prospectus dated Mar. 20, 1996. pp. 1-4, 25-40.
Datascope Corporation, Montvale, NJ, Nov. 1991; 1 PG, American Heart Assoc. Meeting, Anaheim.
Elgiloy Brochure, Jun. 23, 1959; Elgin National Watch Co., Elgin, IL.
Kensey Nash Corporation, Exton, PA, "The Hemostatic Puncture Closure Device", retrieved Oct. 23, 2007, 2 pages.
Laurus Medical Corporation, "Endoscopic Suturing Made Simple," The Laurus ND-2600 Needle Driver, Irvine, CA., Oct. 1994, 1 page.
Marshall, A.C. & Lock, J.E.; "Structural and compliant anatomy of the patent foramen ovale in patients undergoing transcatheter closure", Am. Heart Journ., 140(2):303-307, Aug. 2000.
Nakamura, S. et al., Techniques for Palmaz-Schatz Stent Deployment in Lesions With a Large Side Branch, Catheterization and Cardiovascular Diagnosis, 34: 353-361, 1995.
Product Brochure, "SuperStitch—Closure Made SimpleTM", Sutura, Inc. (2003).
Product Brochure, Laurus Medical Corporation, Irvine, CA "The Laurus In-Line Endoscopic Suturing Device" (Oct. 1994) 1 page.
Rema-Medizintechnik GmbH, Product Brochure entitled "REMA," Apr. 2001, 7 pages.
Serruys, PW et al., A Comparision of Balloon-Expandable-Stent Implantaion With Balloon Angioplasty in Patients With Coronary Artery Disease, New England Journal of Medicine, 331:489-495, 1994.
Taber's Cyclopedic Medical Dictionary, 18th Ed., p. 747, Feb. 1997.
U.S. Appl. No. 07/989,611, May 12, 1993, Office Action.
U.S. Appl. No. 07/989,611, Aug. 1, 1994, Office Action.
U.S. Appl. No. 07/989,611, Nov. 3, 1994, Notice of Allowance.
U.S. Appl. No. 08/148,809, Sep. 16, 1994, Office Action.
U.S. Appl. No. 08/148,809, May 30, 1995, Office Action.
U.S. Appl. No. 08/148,809, Dec. 15, 1995, Notice of Allowance.
U.S. Appl. No. 08/252,124, Jun. 5, 1995, Office Action.
U.S. Appl. No. 08/252,124, Jan. 5, 1996, Office Action.
U.S. Appl. No. 08/252,124, May 22, 1996, Notice of Allowance.
U.S. Appl. No. 08/259,410, Feb. 2, 1995, Office Action.
U.S. Appl. No. 08/259,410, Jun. 1, 1995, Office Action.
U.S. Appl. No. 08/259,410, Feb. 6, 1998, Notice of Allowance.
U.S. Appl. No. 08/638,076, Jan. 21, 1997, Office Action.
U.S. Appl. No. 08/638,076, Oct. 17, 1997, Notice of Allowance.
U.S. Appl. No. 08/824,031, Mar. 16, 1998, Office Action.
U.S. Appl. No. 08/824,031, Sep. 14, 1998, Office Action.
U.S. Appl. No. 08/824,031, Apr. 13, 1999, Office Action.
U.S. Appl. No. 08/824,031, Jul. 15, 1999, Notice of Allowance.
U.S. Appl. No. 08/883,246, Jul. 23, 1998, Office Action.
U.S. Appl. No. 08/883,246, Apr. 12, 1999, Office Action.
U.S. Appl. No. 08/883,246, Oct. 13, 1999, Office Action.
U.S. Appl. No. 08/883,246, Oct. 23, 2000, Office Action.
U.S. Appl. No. 08/883,246, Jul. 11, 2001, Office Action.
U.S. Appl. No. 08/883,246, Sep. 11, 2001, Notice of Allowance.
U.S. Appl. No. 09/057,108, Jul. 10, 2000, Office Action.
U.S. Appl. No. 09/057,108, Oct. 25, 2000, Notice of Allowance.
U.S. Appl. No. 09/262,402, Mar. 29, 2000, Office Action.
U.S. Appl. No. 09/262,402, May 30, 2000, Notice of Allowance.
U.S. Appl. No. 09/395,901, Jun. 27, 2000, Office Action.
U.S. Appl. No. 09/395,901, Nov. 6, 2000, Office Action.
U.S. Appl. No. 09/395,901, Apr. 20, 2001, Notice of Allowance.
U.S. Appl. No. 09/395,901, Sep. 10, 2001, Notice of Allowance.
U.S. Appl. No. 09/610,099, Jul. 11, 2002, Office Action.
U.S. Appl. No. 09/610,099, Dec. 24, 2002, Notice of Allowance.
U.S. Appl. No. 09/651,344, Feb. 28, 2003, Office Action.
U.S. Appl. No. 09/651,344, Nov. 7, 2003, Office Action.
U.S. Appl. No. 09/651,344, Apr. 20, 2004, Notice of Allowance.
U.S. Appl. No. 09/707,746, Feb. 16, 2005, Office Action.
U.S. Appl. No. 09/707,746, Jul. 7, 2005, Office Action.
U.S. Appl. No. 09/707,746, Nov. 15, 2005, Notice of Allowance.
U.S. Appl. No. 09/769,109, Oct. 23, 2001, Office Action.
U.S. Appl. No. 09/769,109, Jun. 17, 2002, Office Action.
U.S. Appl. No. 09/769,109, Sep. 9, 2002, Notice of Allowance.
U.S. Appl. No. 09/988,541, Mar. 17, 2004, Office Action.
U.S. Appl. No. 09/988,541, Feb. 28, 2005, Office Action.
U.S. Appl. No. 09/988,541, May 25, 2005, Office Action.
U.S. Appl. No. 09/988,541, Aug. 24, 2005, Office Action.
U.S. Appl. No. 09/988,541, Nov. 8, 2005, Office Action.
U.S. Appl. No. 09/988,541, Dec. 13, 2005, Notice of Allowance.
U.S. Appl. No. 10/033,689, Sep. 30, 2003, Office Action.
U.S. Appl. No. 10/152,272, Jan. 24, 2005, Office Action.
U.S. Appl. No. 10/152,272, May 13, 2005, Notice of Allowance.
U.S. Appl. No. 10/335,065, Mar. 17, 2005, Office Action.
U.S. Appl. No. 10/335,065, Jun. 10, 2005, Office Action.
U.S. Appl. No. 10/335,065, Nov. 17, 2005, Notice of Allowance.
U.S. Appl. No. 10/335,147, Dec. 13, 2005, Office Action.
U.S. Appl. No. 10/335,147, Apr. 17, 2006, Office Action.
U.S. Appl. No. 10/335,147, Oct. 4, 2006, Notice of Allowance.
U.S. Appl. No. 10/357,984, Jan. 9, 2006, Office Action.
U.S. Appl. No. 10/357,984, Mar. 16, 2006, Office Action.
U.S. Appl. No. 10/357,984, Sep. 28, 2006, Office Action.
U.S. Appl. No. 10/357,984, Mar. 23, 2007, Office Action.
U.S. Appl. No. 10/357,984, Nov. 14, 2007, Office Action.
U.S. Appl. No. 10/652,182, Aug. 9, 2006, Office Action.
U.S. Appl. No. 10/652,182, Feb. 22, 2007, Notice of Allowance.
U.S. Appl. No. 10/660,288, Nov. 15, 2005, Office Action.
U.S. Appl. No. 10/660,288, Mar. 9, 2006, Office Action.
U.S. Appl. No. 10/660,288, Aug. 24, 2006, Office Action.
U.S. Appl. No. 10/660,288, Feb. 1, 2007, Office Action.
U.S. Appl. No. 10/660,288, Jun. 28, 2007, Office Action.
U.S. Appl. No. 10/660,288, Apr. 29, 2009, Office Action.
U.S. Appl. No. 10/660,288, Aug. 3, 2009, Office Action.
U.S. Appl. No. 10/660,288, Mar. 30, 2010, Office Action.
U.S. Appl. No. 10/660,288, Mar. 29, 2011, Office Action.
U.S. Appl. No. 10/660,288, Sep. 30, 2011, Notice of Allowance.
U.S. Appl. No. 10/729,541, Dec. 12, 2006, Office Action.
U.S. Appl. No. 10/729,541, Jun. 18, 2007, Office Action.
U.S. Appl. No. 10/729,541, Jan. 8, 2008, Office Action.
U.S. Appl. No. 10/729,541, Sep. 23, 2008, Office Action.
U.S. Appl. No. 10/729,541, May 1, 2009, Office Action.
U.S. Appl. No. 10/729,541, Nov. 16, 2009, Notice of Allowance.
U.S. Appl. No. 10/729,541, Mar. 25, 2010, Notice of Allowance.
U.S. Appl. No. 10/729,541, Jul. 12, 2010, Notice of Allowance.
U.S. Appl. No. 10/729,541, Nov. 3, 2010, Issue Notification.
U.S. Appl. No. 10/737,668, Nov. 2, 2005, Office Action.
U.S. Appl. No. 10/737,668, Feb. 16, 2006, Office Action.
U.S. Appl. No. 10/737,668, Oct. 19, 2006, Office Action.
U.S. Appl. No. 10/737,668, Jun. 7, 2007, Office Action.
U.S. Appl. No. 10/737,668, Nov. 28, 2007, Office Action.
U.S. Appl. No. 10/737,668, Jun. 26, 2008, Notice of Allowance.
U.S. Appl. No. 10/742,406, Mar. 23, 2007, Office Action.
U.S. Appl. No. 10/742,406, Sep. 10, 2007, Notice of Allowance.
U.S. Appl. No. 10/742,406, Jan. 11, 2008, Notice of Allowance.
U.S. Appl. No. 10/746,210, Apr. 5, 2007, Office Action.
U.S. Appl. No. 10/746,210, Aug. 21, 2007, Office Action.
U.S. Appl. No. 10/746,210, Jul. 9, 2008, Notice of Allowance.
U.S. Appl. No. 10/813,449, Sep. 5, 2006, Office Action.
U.S. Appl. No. 10/813,449, Jul. 16, 2007, Office Action.
U.S. Appl. No. 10/813,449, Jan. 25, 2008, Office Action.
U.S. Appl. No. 10/813,449, Aug. 14, 2008, Office Action.
U.S. Appl. No. 10/813,449, Sep. 15, 2008, Office Action.
U.S. Appl. No. 10/813,449, Feb. 3, 2009, Office Action.
U.S. Appl. No. 10/813,449, Aug. 28, 2009, Office Action.
U.S. Appl. No. 10/813,449, May 27, 2010, Office Action.
U.S. Appl. No. 10/909,531, Apr. 4, 2007, Office Action.
U.S. Appl. No. 10/909,531, Dec. 26, 2007, Office Action.
U.S. Appl. No. 10/909,531, Jun. 13, 2008, Office Action.
U.S. Appl. No. 10/909,531, Feb. 9, 2009, Office Action.
U.S. Appl. No. 10/909,531, Sep. 16, 2009, Office Action.
U.S. Appl. No. 10/909,531, Apr. 29, 2010, Notice of Allowance.
U.S. Appl. No. 10/909,531, Aug. 20, 2010, Notice of Allowance.
U.S. Appl. No. 10/909,531, Nov. 23, 2010, Issue Notification.
U.S. Appl. No. 10/948,445, Jul. 11, 2007, Office Action.
U.S. Appl. No. 11/199,338, Jan. 25, 2007, Office Action.

(56) References Cited

OTHER PUBLICATIONS

U.S. Appl. No. 11/199,338, Oct. 5, 2007, Office Action.
U.S. Appl. No. 11/199,338, Dec. 28, 2007, Office Action.
U.S. Appl. No. 11/199,338, Apr. 23, 2008, Office Action.
U.S. Appl. No. 11/199,338, Jan. 6, 2009, Office Action.
U.S. Appl. No. 11/199,496, Apr. 1, 2009, Office Action.
U.S. Appl. No. 11/199,496, Aug. 21, 2009, Office Action.
U.S. Appl. No. 11/199,496, Apr. 23, 2010, Office Action.
U.S. Appl. No. 11/199,496, Apr. 28, 2011, Office Action.
U.S. Appl. No. 11/199,496, Aug. 18, 2011, Notice of Allowance.
U.S. Appl. No. 11/199,515, Aug. 20, 2008, Office Action.
U.S. Appl. No. 11/199,515, Nov. 13, 2008, Office Action.
U.S. Appl. No. 11/199,515, Jun. 10, 2009, Office Action.
U.S. Appl. No. 11/199,515, Dec. 24, 2009, Notice of Allowance.
U.S. Appl. No. 11/199,515, Apr. 2, 2010, Notice of Allowance.
U.S. Appl. No. 11/199,515, Aug. 2, 2010, Notice of Allowance.
U.S. Appl. No. 11/273,107, Jun. 14, 2007, Office Action.
U.S. Appl. No. 11/273,107, Jan. 18, 2008, Office Action.
U.S. Appl. No. 11/273,107, Sep. 5, 2008, Office Action.
U.S. Appl. No. 11/273,107, Apr. 9, 2009, Office Action.
U.S. Appl. No. 11/273,107, Oct. 28, 2009, Office Action.
U.S. Appl. No. 11/273,107, Jun. 2, 2010, Office Action.
U.S. Appl. No. 11/273,107, Oct. 27, 2010, Office Action.
U.S. Appl. No. 11/273,107, Jun. 2, 2011, Notice of Allowance.
U.S. Appl. No. 11/363,005, Jun. 22, 2007, Office Action.
U.S. Appl. No. 11/363,005, Dec. 14, 2007, Office Action.
U.S. Appl. No. 11/363,005, Apr. 17, 2008, Office Action.
U.S. Appl. No. 11/363,005, Dec. 23, 2008, Office Action.
U.S. Appl. No. 11/363,005, Jul. 10, 2009, Notice of Allowance.
U.S. Appl. No. 11/363,005, Jan. 14, 2010, Notice of Allowance.
U.S. Appl. No. 11/363,005, Jul. 23, 2010, Notice of Allowance.
U.S. Appl. No. 11/363,005, Nov. 10, 2010, Issue Notification.
U.S. Appl. No. 11/389,762, Sep. 20, 2007, Notice of Allowance.
U.S. Appl. No. 11/389,762, Nov. 23, 2007, Notice of Allowance.
U.S. Appl. No. 11/390,937, Sep. 7, 2007, Office Action.
U.S. Appl. No. 11/391,951, Oct. 28, 2008, Office Action.
U.S. Appl. No. 11/391,951, Jan. 30, 2009, Office Action.
U.S. Appl. No. 11/391,951, Aug. 26, 2009, Office Action.
U.S. Appl. No. 11/391,951, Jun. 23, 2010, Office Action.
U.S. Appl. No. 11/465,527, Feb. 3, 2010, Office Action.
U.S. Appl. No. 11/465,527, Jul. 23, 2010, Notice of Allowance.
U.S. Appl. No. 11/465,527, Nov. 10, 2010, Issue Notification.
U.S. Appl. No. 11/552,593, Aug. 21, 2008, Office Action.
U.S. Appl. No. 11/552,593, Feb. 5, 2009, Office Action.
U.S. Appl. No. 11/552,593, Oct. 13, 2009, Notice of Allowance.
U.S. Appl. No. 11/552,593, Mar. 22, 2010, Notice of Allowance.
U.S. Appl. No. 11/552,593, Jul. 22, 2010, Notice of Allowance.
U.S. Appl. No. 11/552,593, Nov. 10, 2010, Issue Notification.
U.S. Appl. No. 11/688,722, Mar. 10, 2010, Office Action.
U.S. Appl. No. 11/688,722, Jul. 29, 2010, Notice of Allowance.
U.S. Appl. No. 11/688,722, Nov. 17, 2010, Issue Notification.
U.S. Appl. No. 11/891,358, Apr. 26, 2010, Office Action.
U.S. Appl. No. 11/891,358, Oct. 19, 2010, Office Action.
U.S. Appl. No. 11/891,358, Aug. 31, 2011, Office Action.
U.S. Appl. No. 11/891,358, Nov. 18, 2011, Notice of Allowance.
U.S. Appl. No. 11/891,358, Apr. 10, 2012, Notice of Allowance.
U.S. Appl. No. 11/891,513, Apr. 9, 2010, Office Action.
U.S. Appl. No. 11/891,513, Sep. 28, 2010, Office Action.
U.S. Appl. No. 11/891,513, Aug. 31, 2011, Office Action.
U.S. Appl. No. 11/891,513, Nov. 1, 2011, Notice of Allowance.
U.S. Appl. No. 11/891,513, May 8, 2012, Notice of Allowance.
U.S. Appl. No. 11/960,593, Sep. 14, 2010, Office Action.
U.S. Appl. No. 11/960,593, Nov. 3, 2010, Office Action.
U.S. Appl. No. 11/960,593, Apr. 28, 2011, Office Action.
U.S. Appl. No. 11/997,379, Jul. 13, 2011, Office Action.
U.S. Appl. No. 11/997,379, Feb. 28, 2012, Office Action.
U.S. Appl. No. 11/997,379, May 11, 2012, Notice of Allowance.
U.S. Appl. No. 12/182,836, Oct. 5, 2010, Office Action.
U.S. Appl. No. 12/182,836, Jun. 23, 2011, Office Action.
U.S. Appl. No. 12/247,012, Oct. 13, 2011, Office Action.
U.S. Appl. No. 12/247,012, Mar. 16, 2012, Office Action.
U.S. Appl. No. 12/247,012, Aug. 13, 2012, Notice of Allowance.
U.S. Appl. No. 12/257,127, Aug. 30, 2010, Office Action.
U.S. Appl. No. 12/257,127, Dec. 22, 2010, Office Action.
U.S. Appl. No. 12/257,127, Jul. 6, 2011, Office Action.
U.S. Appl. No. 12/257,127, Jan. 12, 2012, Office Action.
U.S. Appl. No. 12/257,127, Sep. 20, 2012, Notice of Allowance.
U.S. Appl. No. 12/334,077, Oct. 27, 2010, Office Action.
U.S. Appl. No. 12/334,077, Jul. 21, 2011, Office Action.
U.S. Appl. No. 12/334,085, Dec. 23, 2010, Office Action.
U.S. Appl. No. 12/334,085, Aug. 4, 2011, Office Action.
U.S. Appl. No. 12/334,085, Jan. 9, 2012, Notice of Allowance.
U.S. Appl. No. 12/873,728, Sep. 11, 2012, Office Action.
U.S. Appl. No. 12/950,338, Jun. 15, 2011, Office Action.
U.S. Appl. No. 12/950,338, Nov. 1, 2011, Notice of Allowance.
U.S. Appl. No. 12/950,338, Aug. 8, 2012, Notice of Allowance.
U.S. Appl. No. 12/955,848, Jun. 30, 2011, Office Action.
U.S. Appl. No. 12/955,848, Nov. 15, 2011, Office Action.
U.S. Appl. No. 12/955,863, Jan. 6, 2012, Office Action.
U.S. Appl. No. 12/955,863, May 15, 2012, Notice of Allowance.
U.S. Appl. No. 12/955,869, Oct. 18, 2011, Office Action.
U.S. Appl. No. 12/955,869, Mar. 22, 2012, Notice of Allowance.
U.S. Appl. No. 12/961,239, Jul. 26, 2011, Notice of Allowance.
U.S. Appl. No. 12/966,961, Aug. 18, 2011, Notice of Allowance.
U.S. Appl. No. 13/022,050, Jul. 11, 2011, Office Action.
U.S. Appl. No. 13/022,050, Apr. 26, 2012, Office Action.
U.S. Appl. No. 13/022,050, Jul. 6, 2012, Notice of Allowance.
U.S. Appl. No. 90/006,469, Nov. 29, 2002, Request for Re-Examination.
U.S. Appl. No. 90/006,469, Sep. 10, 2004, Office Action.
U.S. Appl. No. 90/006,469, Sep. 27, 2005, Notice of Re-Issue.
U.S. Appl. No. 90/006,469, Jun. 27, 2006, Re-Examination Certification.
U.S. Appl. No. 12/257,127, Jan. 9, 2013, Issue Notification.
U.S. Appl. No. 13/593,154, Jan. 8, 2013, Notice of Allowance.
U.S. Appl. No. 13/870,628, filed Apr. 25, 2013, Ma.
U.S. Appl. No. 12/873,728, May 3, 2013, Office Action.
U.S. Appl. No. 12/182,836, May 17, 2013, Office Action.
U.S. Appl. No. 13/615,530, Jun. 12, 2013, Notice of Allowance.
U.S. Appl. No. 11/960,593, Jul. 1, 2013, Notice of Allowance.
U.S. Appl. No. 12/950,338, Nov. 14, 2012, Issue Notification.
U.S. Appl. No. 13/022,050, Oct. 31, 2012, Issue Notification.
U.S. Appl. No. 13/752,095, filed Jan. 28, 2013, McIntosh.
U.S. Appl. No. 12/247,012, Mar. 27, 2013, Issue Notification.
U.S. Appl. No. 13/593,154, Apr. 10, 2013, Issue Notification.
U.S. Appl. No. 12/334,077, Jan. 16, 2013, Office Action.
U.S. Appl. No. 13/615,530, Jan. 17, 2013, Office Action.
U.S. Appl. No. 12/334,077, Oct. 11, 2013, Notice of Allowance.
U.S. Appl. No. 12/334,077, Feb. 13, 2014, Issue Notification.
U.S. Appl. No. 12/873,728, Aug. 23, 2013, Office Action.
U.S. Appl. No. 12/873,728, Nov. 4, 2013, Notice of Allowance.
U.S. Appl. No. 12/873,728, Feb. 13, 2014, Issue Notification.
U.S. Appl. No. 13/455,053, Nov. 27, 2013, Office Action.
Definition of "pair", Dictionary.com, accessed on May 5, 2014.
U.S. Appl. No. 13/455,053, Jun. 9, 2014, Notice of Allowance.
U.S. Appl. No. 13/525,875, May 28, 2014, Office Action.

\* cited by examiner

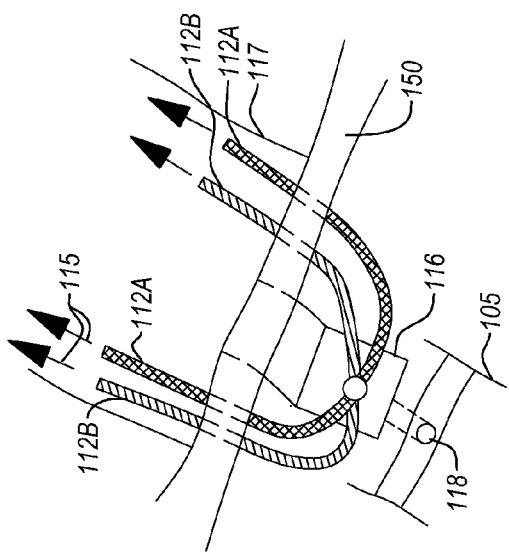
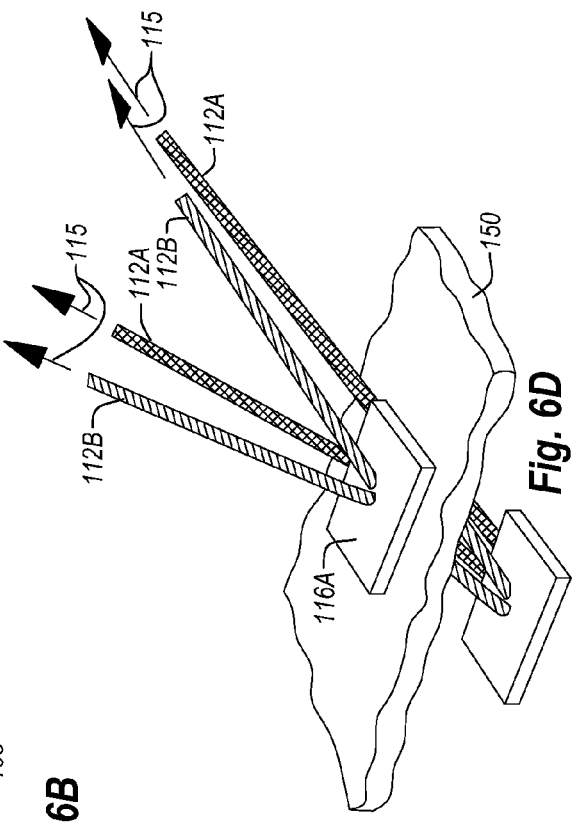
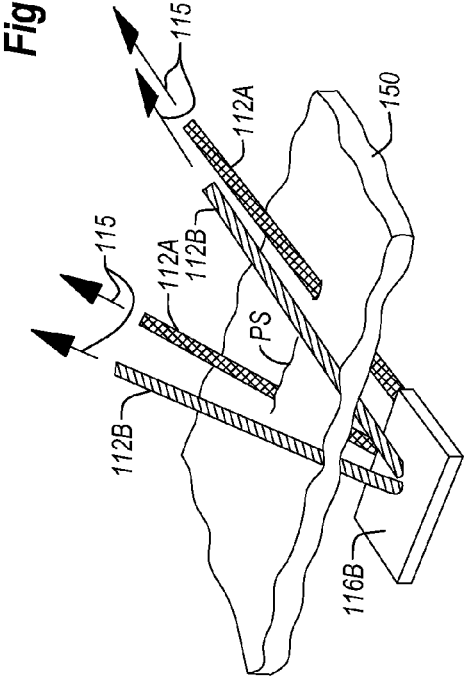

APPARATUS AND METHOD FOR SUTURING BODY LUMENS

BACKGROUND

1. Technical Field

The present disclosure relates generally to techniques and devices for closing openings in body lumens. More particularly, the present disclosure relates to systems, devices, and methods for percutaneous closure of arterial and venous puncture sites, which are usually accessed through a tissue tract.

2. The Relevant Technology

Many diagnostic and interventional vascular procedures are now performed translumenally. A catheter is introduced to the vascular system at a convenient access location and guided through the vascular system to a target location using established techniques. Such procedures require vascular access, which is usually established using the well-known Seldinger technique. Vascular access is generally provided through an introducer sheath, which is positioned to extend from outside the patient's body into the vascular lumen. When vascular access is no longer required, the introducer sheath is removed and bleeding at the puncture site is stopped using one of a variety of methods.

One method for providing hemostasis (the cessation of bleeding) is to apply external force near and upstream from the puncture site, typically by manual compression. This approach suffers from a number of disadvantages. For example, the manual compression procedure is time consuming, frequently requiring 30 or more minutes of compression before hemostasis is achieved. Additionally, such compression techniques rely on clot formation, which can be delayed until anticoagulants used in vascular therapy procedures (such as for heart attacks, stent deployment, non-optical PTCA results, and the like) wear off. The anticoagulants may take two to four hours to wear off, thereby increasing the time required before completion of the manual compression procedure.

Further, the manual compression procedure is uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to twelve hours or more under close observation to assure continued hemostasis. During this time, renewed bleeding may occur, resulting in blood loss through the tract, hematoma and/or pseudo-aneurysm formation, as well as arteriovenous fistula formation. These complications may require blood transfusions and/or surgical intervention.

The incidence of complications from the manual compression procedure increases when the size of the introducer sheath grows larger, and/or when the patient is anticoagulated. The compression technique for arterial closure can be risky, and is expensive and onerous to the patient. Although using highly trained individuals can reduce the risk of complications, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

To overcome the problems associated with manual compression, bioabsorbable sealing bodies have been used. Generally, a thrombogenic and bioabsorbable material, such as collagen, is placed at the superficial wall of the body lumen over the puncture site. While potentially effective, this approach suffers from a number of drawbacks. For example, bioabsorbable sealing bodies may lack a solid mechanical attachment of the sealing body to the tissue. Due to the lack of a solid mechanical attachment, the sealing body can wander within the tissue tract or move out of the puncture site, thus causing late bleeds. Conversely, if the sealing body wanders and intrudes too far into the body lumen, due to the lack of a solid mechanical attachment, intravascular clots and/or collagen pieces with thrombus attached can form and embolize downstream, causing vascular occlusion.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Embodiments described herein provide systems, methods, and devices for closing an opening in tissue. Embodiments can be configured to close an opening within a body lumen.

For instance, in one embodiment, an apparatus for suturing a body lumen includes a flexible elongated member that has a proximal end, a distal end, a central passage and multiple needle lumens extending from the proximal end toward the distal end. The flexible elongated member further includes an elongated subsection spanning from the end of the needle lumens in the elongated member to a barrel portion that includes corresponding needle lumens on the proximal end of the elongated member. The elongated subsection provides sufficient space between the needles and the barrel portion to allow transapical insertion of the elongated member into a body lumen. The apparatus further includes multiple different needles disposed within and advanceable from the needle lumens in the flexible elongated member across the elongated subsection to corresponding needle lumens in the barrel portion. The apparatus also includes a handle disposed at the proximal end of the elongated member. The handle is operable to retract the needles through the needle lumens of the elongated member across the elongated subsection toward the handle at the proximal end.

In another embodiment, a method is provided for suturing an opening in a body lumen. The method includes providing a body lumen suturing device, where the body lumen suturing device includes a flexible elongated member that has a proximal end, a distal end, a central passage and multiple needle lumens extending from the proximal end toward the distal end. The flexible elongated member includes an elongated subsection spanning from the end of the needle lumens in the elongated member to a barrel portion that includes corresponding needle lumens on the proximal end of the elongated member. The elongated subsection provides sufficient space between the needles and the barrel portion to allow transapical insertion of the elongated member. The body lumen suturing device further includes needles disposed within and advanceable from the needle lumens in the flexible elongated member across the elongated subsection to corresponding needle lumens in the barrel portion, as well as a handle disposed at the proximal end of the elongated member, where the handle is operable to retract the needles through the needle lumens of the elongated member across the elongated subsection toward the handle at the proximal end.

In yet another embodiment, a body lumen suturing device includes a flexible elongated member having a proximal end, a distal end, a central passage and multiple needle lumens extending from the proximal end toward the distal end. The flexible elongated member further includes an elongated subsection spanning from the end of the needle lumens in the elongated member to a barrel portion that includes corresponding needle lumens on the proximal end of the elongated member. The elongated subsection provides sufficient space between the needles and the barrel portion to allow transapical insertion of the elongated member. The elongated member also includes a crimp ring configured to hold pledgets in place at the proximal end of the needle lumens in the elongated member. The device also includes needles disposed within and advanceable from the needle lumens in the flexible elongated member across the elongated subsection to corresponding needle lumens in the barrel portion, as well as one or more pledgets stored at the proximal end of the needle lumens in the elongated member. The pledgets include holes through which the sutures may be pulled. The device also includes a handle disposed at the proximal end of the elongated member, where the handle is operable to retract the needles through the needle lumens of the elongated member across the elongated subsection toward the handle at the proximal end.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

To further clarify the above and other advantages and features of embodiments of the present invention, a more particular description of embodiments of the present invention will be rendered by reference to the appended drawings. It is appreciated that these drawings depict only typical embodiments of the invention and are therefore not to be considered limiting of its scope. The invention will be described and explained with additional specificity and detail through the use of the accompanying drawings in which:

FIGS. 6A-6D illustrate various embodiments of the suturing device that implement pledgets.

DETAILED DESCRIPTION

Figure 1:
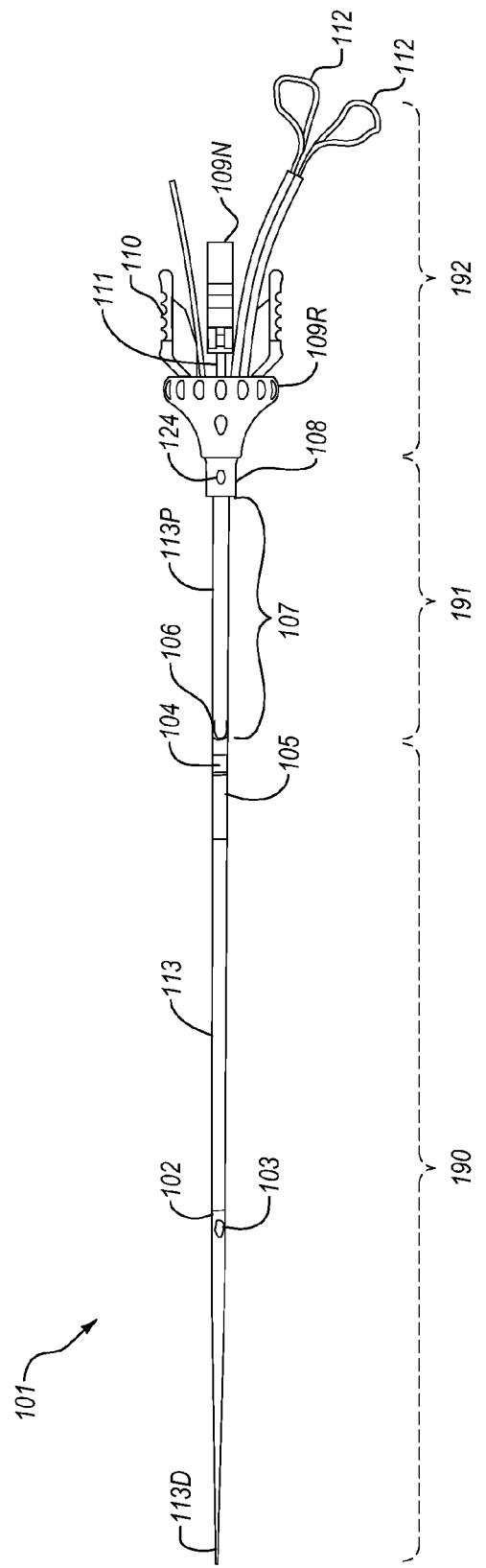
FIG. 1 illustrates a side view of an example embodiment of the suturing device.

Embodiments described herein provide systems, methods, and devices for closing an opening in tissue. Embodiments can be configured to close an opening within a body lumen. For instance, in one embodiment, an apparatus for suturing a body lumen includes a flexible elongated member that has a proximal end, a distal end, a central passage and multiple needle lumens extending from the proximal end toward the distal end. The flexible elongated member further includes an elongated subsection spanning from the end of the needle lumens in the elongated member to a barrel portion that includes corresponding needle lumens on the proximal end of the elongated member. The elongated subsection provides sufficient space between the needles and the barrel portion to allow transapical insertion of the elongated member into a body lumen. The apparatus further includes multiple different needles disposed within and advanceable from the needle lumens in the flexible elongated member across the elongated subsection to corresponding needle lumens in the barrel portion. The apparatus also includes a handle disposed at the proximal end of the elongated member. The handle is operable to retract the needles through the needle lumens of the elongated member across the elongated subsection toward the handle at the proximal end.

In another embodiment, a method is provided for suturing an opening in a body lumen. The method includes providing a body lumen suturing device, where the body lumen suturing device includes a flexible elongated member that has a proximal end, a distal end, a central passage and multiple needle lumens extending from the proximal end toward the distal end. The flexible elongated member includes an elongated subsection spanning from the end of the needle lumens in the elongated member to a barrel portion that includes corresponding needle lumens on the proximal end of the elongated member. The elongated subsection provides sufficient space between the needles and the barrel portion to allow transapical insertion of the elongated member. The body lumen suturing device further includes needles disposed within and advanceable from the needle lumens in the flexible elongated member across the elongated subsection to corresponding needle lumens in the barrel portion, as well as a handle disposed at the proximal end of the elongated member, where the handle is operable to retract the needles through the needle lumens of the elongated member across the elongated subsection toward the handle at the proximal end.

In yet another embodiment, a body lumen suturing device includes a flexible elongated member having a proximal end, a distal end, a central passage and multiple needle lumens extending from the proximal end toward the distal end. The flexible elongated member further includes an elongated subsection spanning from the end of the needle lumens in the elongated member to a barrel portion that includes corresponding needle lumens on the proximal end of the elongated member. The elongated subsection provides sufficient space between the needles and the barrel portion to allow transapical insertion of the elongated member. The elongated member also includes a crimp ring configured to hold pledgets in place at the proximal end of the needle lumens in the elongated member. The device also includes needles disposed within and advanceable from the needle lumens in the flexible elongated member across the elongated subsection to corresponding needle lumens in the barrel portion, as well as one or more pledgets stored at the proximal end of the needle lumens in the elongated member. The pledgets include holes through which the sutures may be pulled. The device also includes a handle disposed at the proximal end of the elongated member, where the handle is operable to retract the needles through the needle lumens of the elongated member across the elongated subsection toward the handle at the proximal end.

As used herein, the term "distal" is generally defined as in the direction of the patient, or away from a user of a device, or in a downstream direction relative to a forward flow of blood. In the context of a medical device intervention with or through a vessel wall, "distal" herein refers to the interior or the lumen side of the vessel wall.

Conversely, "proximal" generally means away from the patient, or toward the user, or in an upstream direction relative to a forward flow of blood. In the context of a medical device intervention with or through a vessel wall, "proximal" herein refers to the exterior or outer side of the vessel wall.

Additionally, "oblong" is herein intended to mean oval, elliptical, or otherwise having a generally rounded shape that is not perfectly circular. In particular, the term describes the shape of a tubular graft end cut at an acute angle relative to the plane perpendicular to the tissue walls defining the graft.

The term "hemostasis" is herein used to mean the arrest of bleeding or substantially blocking flow of blood outwardly from a vessel lumen while the vessel lumen is pressurized or sustaining physiological blood flow. This amount of blockage or occlusion to flow is further defined such that the blood loss which is experienced is less than an amount which would affect procedural methods or outcomes according to a physician user of a device of ordinary skill in the art. In other words, "hemostasis" is not intended to mean only "total hemostasis" such that there is a total lack of blood loss. Rather, the term is used to also mean "procedural hemostasis" as a relative term in its use among physicians of ordinary skill.

Similarly, "occlusion," "occlude," "blockage," "block . . . plugging", "block," or variations thereof are all terms which are herein intended to have a procedurally relevant definition in the context of their use. For instance, an aperture is "occluded" although there is some measurable flow therethrough, but that flow is so low such that the intended procedural benefit of occlusion is at least partially achieved. Certainly, such terms also properly include within their scope a "total effect" definition, as well.

The term "perfusion" is herein used to mean the flow of blood or other unit of perfusate (the fluid used for perfusion) per unit volume of tissue. Physiological perfusion refers to the amount of blood flow present when the body is functioning normally. For example, physiological perfusion usually prevents clinically significant ST elevations which is one of the most sensitive indicators of inadequate perfusion. Adequate perfusion refers to the amount of blood flow that avoids the clinical requirement of transfusing the patient or that is needed to prevent tissue necrosis distal to the aperture in the blood vessel.

The term "suturing" is herein intended to include the process of joining two surfaces or edges together with a fastener so as to close an aperture, opening, or wound or join tissues. The fastener is usually a suture such as a thread of material (either polymeric or natural), gut, wire or the like. The term fastener as used herein also includes clamps, studs, hasps, catches, hooks, rivets, staples, snaps, stitches, VELCROC, buttons, and other coupling members.

As shown in FIG. 1, a tissue suturing device 101 may be provided to close openings in body tissues. The tissue suturing device 101 includes multiple different parts. These parts may be generally divided into three sections including a handle section 192, a substantially rigid intermediate section 191, and a flexible elongated section 190. Each section may include different sub-parts that are each designed to provide an intended portion of functionality.

The handle section 192 of the tissue suturing device 101 includes a hand grip 110 and rotatable handle portion 109R. The hand grip and rotatable handle portion allow a physician or other user to hold and manipulate the tissue suturing device 101. For example, the physician can hold on to the hand grip 110 and the rotatable handle portion 109R when inserting or withdrawing the tissue suturing device from a body lumen. The handle section 192 also includes an actuating member 109N which is mechanically linked to the needles 115 (FIGS. 4A-5) in the elongated member 113. When the handle 109N is pulled, the mechanical link to the needles is actuated and the needles are drawn from the distal end 113D of the elongated member 113 toward the proximal end 113P of the elongated member 113. As will be shown further in regard to FIGS. 2 and 3, the handle 109N is mechanically linked to a support holster 121 which holds the needles within the sheath 105. When the handle 109N is pulled toward the user, the support holster moves, along with the needles, through the sheath 105 and toward the handle.

The substantially rigid intermediate section 191 extends from the rotatable handle portion 109R to the needle guide 106. This intermediate section includes a barrel portion 108 which routes the needles 115 through the barrel and out toward the handle portion 192. The needles 115 carry sutures 112 which are used to close openings in the tissue. The needles extend from the needle guide 106 through any intervening tissue toward the barrel portion 108. The barrel portion captures the needles and routes them through an opening 124 toward the user. The substantially rigid intermediate section 191 also includes elongated subsection 107 which spans a tissue gap. This tissue gap comprises the tissue area through which the elongated subsection is inserted. The elongated subsection allows for the tissue suturing device 101 to be inserted transapically into the heart or into other bodily tissues. In some embodiments, the elongated subsection 107 may allow a user to insert the device transapically and perform a percutaneous closure of the left ventricle of the heart. This embodiment will be explained in greater detail below.

The flexible elongated portion 190 of the tissue suturing device 101 includes the needles 115 (shown in FIGS. 2-5), a guidewire port for advancing the device along a guidewire 114 (shown in FIG. 2) and a flexible outer sheath 105. The flexible elongated portion 190 may be inserted entirely into the body lumen using the guidewire to advance the device. Once the tissue suturing device has been inserted into the vascular tissue, the guidewire can be removed by the operator. The sheath 105 of the elongated member 113 supports various internal structures including the needle holder 102 (FIG. 1). The flexibility of the elongated portion allows the elongated portion to be inserted in a variety of different types and sizes of tissues, including into arteries (such as the femoral artery) and into the heart.

Figure 5:
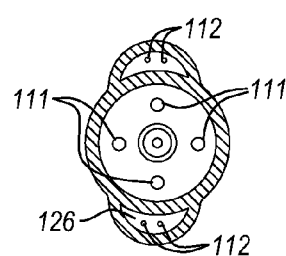
FIG. 5. is a cross-sectional view of the device of FIGS. 4A and 4B, taken along line 3-3 of FIG. 4B.

The needle holder 102 of the flexible elongated portion 190 may be configured to hold one or more needles within needle lumens 119 which are axially aligned and spaced about the interior of the elongated member 113 (as shown in FIG. 5). The needle support holster 121, upon actuation of the handle 109, may be advanced up the needle shaft 111 toward the proximal end 113P of the elongated member 113. As the needle support holster 121 is advanced, the needles 115 held by the needle support holster 121 are correspondingly advanced toward the needle shaft 111 in the handle 109. The needles are withdrawn through the needle guide 106 toward the barrel portion 108. As will be explained in greater detail with regard to FIG. 7, the barrel portion 108 includes two semi-circular openings 160 that receive the needles 115, even in cases where the needles 115 are drawn through relatively large tissue gaps.

Thus, the flexible elongated portion 190 houses the needles 115 which will be drawn toward the handle 109 of the tissue suturing device 101. The needles 115 are withdrawn along needle guide 106 and across the tissue gap covered by elongated subsection 107 toward the barrel portion 108. While being advanced from the needle guide 106 to the barrel portion 108, the needles may exhibit a tendency to deflect or travel away from the tissue suturing device 101. For example, in cases where the tissue suturing device 101 is inserted transapically into the left ventricle of the heart, the tissue suturing device will be inserted through body tissue that is thicker and/or tougher than the body tissue typically involved in a femoral arteriotomy. For instance, the tissue gap in a transapical insertion may be 1-5 cm. In a femoral arteriotomy, a tissue suturing device is placed through skin and muscle tissue in the leg, and ultimately through the femoral artery. In a transapical insertion, the tissue suturing device is inserted near or through the ribcage toward the heart. This tissue near the ribcage and heart is often fibrous and tough, and may cause the needles to deflect and travel away from the tissue suturing device. Accordingly, larger, semi-circular openings 160 are provided in the barrel portion 108 to capture the needles 115 as they approach the handle portion 109.

Thus, to compensate for the thicker, more fibrous tissue through which the tissue suturing device 101 will be inserted, a tissue suturing device with a substantially rigid elongated subsection 107 is provided. The elongated subsection 107 provides sufficient space between the needle guides 106 and the needle-receiving barrel portion to allow transapical insertion of the device 101. The needles 115 are drawn through the tissue and across the tissue gap provided by the elongated subsection 107. The elongated subsection 107 is specifically designed to provide sufficient space between the needles 115 and the barrel portion 108 to allow transapical insertion of the elongated member 113. This is show in greater detail in FIGS. 2-4. It should be noted that although the tissue suturing device is usable for transapical insertion into a heart ventricle, it will be appreciated that the tissue suturing device 101 can be readily adapted for use with punctures made to other hollow body organs and lumens. It may, however, be necessary to modify the dimensions and other particular aspects of the tissue suturing device to accommodate the different usage environments.

Referring now to FIGS. 2, 4A, 4B, and 5, a tissue suturing device 101 is provided which is suitable for suturing and sealing of a percutaneous vascular puncture site (particularly those made transapically to the left ventricle of the heart), the tissue suturing device 101 having an alternate handle illustrated in phantom. The tissue suturing device 101 comprises an elongated member 113 and a needle shaft 111. The elongated member 113 includes a guide tip 123 at its distal end of the substantially rigid intermediate section 191. The guide tip includes a plurality of guide channels 125 which receive the proximal ends of needles 115. The needles 115, as illustrated, comprise a sharpened tip section 115A and an elongated shank portion 122, but may also be manufactured as an integral piece. The shank portion 122 may be sufficiently long so that the needles may be pushed from their butt end by a support holster 121 fixedly attached to the needle shaft 111. By withdrawing the handle 109N (FIG. 1 or FIG. 2), the mechanically linked support holster 121 is also withdrawn toward the user, carrying the needles 115 and pushing the needles through the intervening tissue. The needles may be withdrawn until they enter the barrel portion 108 and exit through the barrel opening 124.

The elongated member 113 further includes a plurality of needle lumens 119 which are axially aligned and spaced about the periphery of the elongated member. As shown in FIGS. 4B and 5, the needles 115 are designed to enter the distal ends of the lumens 119 as the needles are advanced proximally relative to the elongated member 113. A flexible needle sheath (channel guide) 105 is attached to the guide tip 123 of the elongated member 113. The central lumen of the needle sheath 105 receives a support holster 121 attached to the distal end of the needle shaft 111, as well as the needles 115. The butts of the needles 115 are removably received within the support holster 121. The sheath 105 is designed to be sufficiently long to permit the needles to extend at least 5 cm beyond the distal end of elongated subsection 107 and into the barrel portion 108.

Figure 4A:
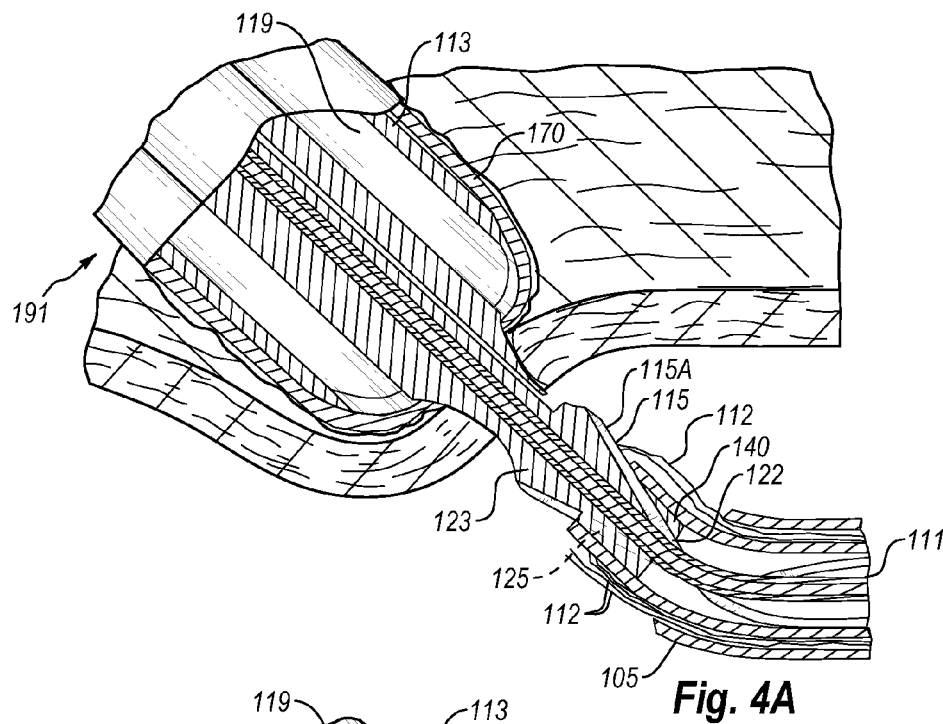
FIG. 4A is a detailed view of the distal end of the guide body of the suturing device of FIG. 2, shown with the needles retracted fully within the guide body.
Figure 4B:
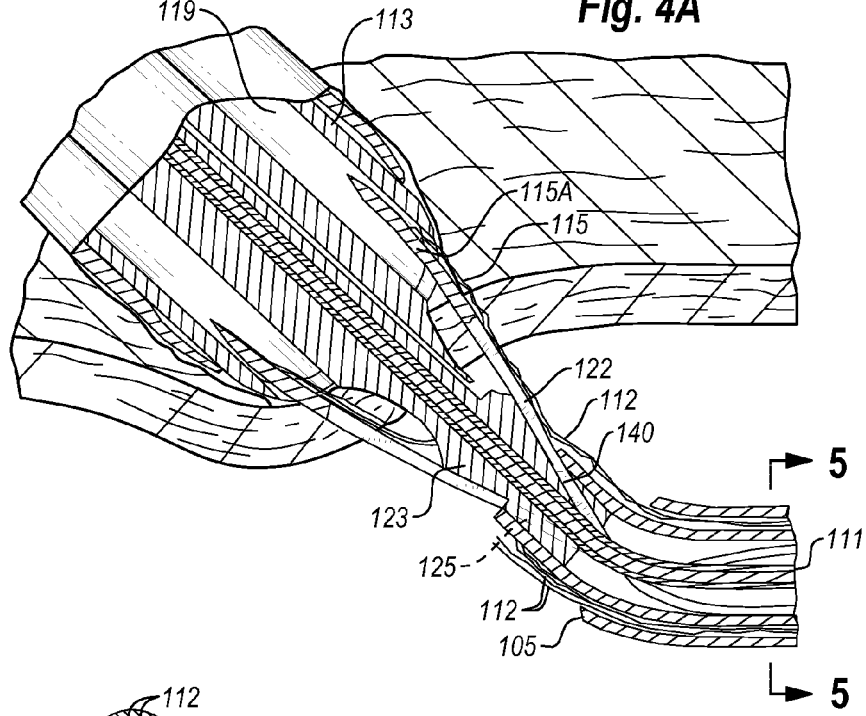
FIG. 4B is a detailed view similar to FIG. 4A, except that the needles have been partially deployed.

Prior to use, the suture applying device 101 will be in the configuration illustrated in FIGS. 1 and 4A. That is, the needle shaft 111 will be distally positioned within the elongated member 113 and needle sheath 105. In particular, the tips of needles 115A will lie just at the guide tip 123 so that they may be easily advanced through the vascular tissue of the heart, as well as any surrounding tissue. That is, the tips of the needles 115A will be generally retracted within the guide tip 123. A length of suture 112 is attached to the proximal tips 115A of opposed pairs of needles 115, with the connecting suture being stored within side lumens 126 extending axially along the exterior of the needle sheath 105.

As best observed in FIGS. 4A, 4B and 5, the suture 112 extending between one pair of opposed needles is received in a first of the side lumens 126, while the suture extending between the other pair of opposed needles is received in the second of the side lumens 126. In some embodiments, the sutures 112 may be stored in the lumens 119 of the elongated member 113 (and thus eliminate the need for side lumens 126). The use of side lumens 126 may simplify feeding of the suture as the needles 115 are withdrawn.

After the guide tip 123 has been passed through the puncture site to be sutured, the needles may then be drawn proximally forward through the tissue to be sutured by drawing proximally on handle 109 at the proximal end of needle shaft 111. Methods described herein for suturing an opening in a body lumen will now be described in more detail with reference to FIGS. 2-4.

Figure 2:
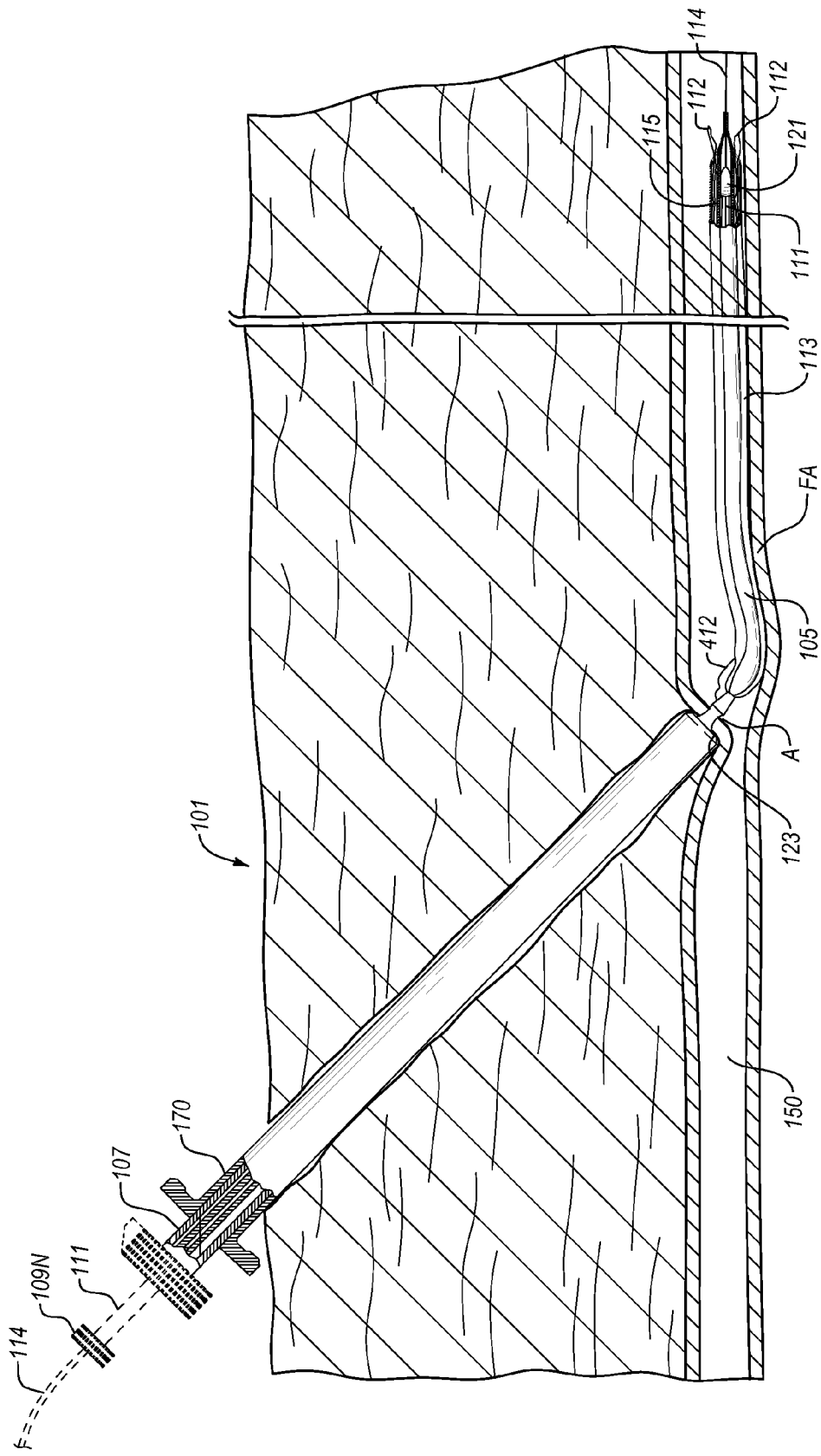
FIG. 2 illustrates insertion of the elongate member and barrel portion.
Figure 3:
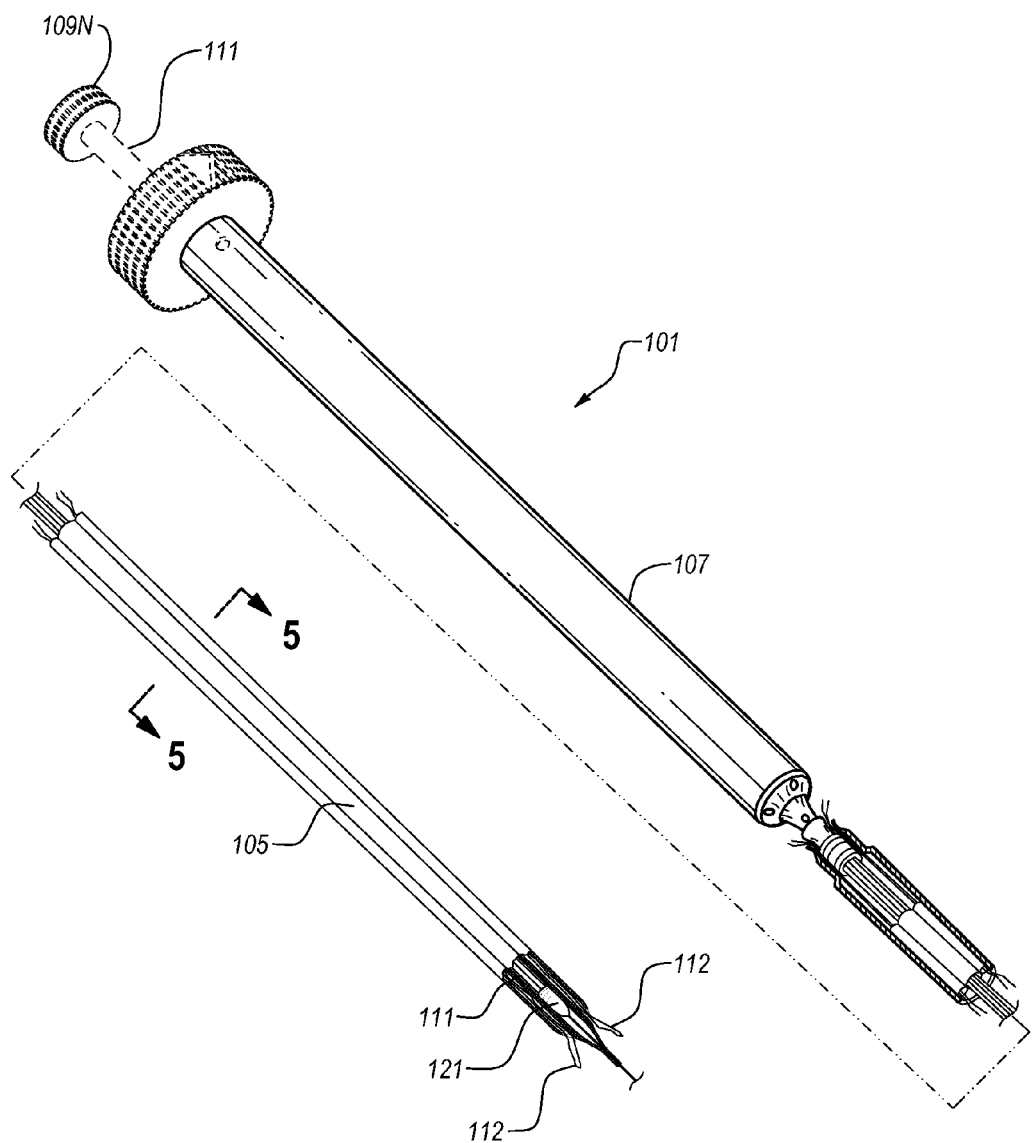
FIG. 3 is a perspective view of an example embodiment of a suturing device.

The situation following an interventional or other vascular procedure, where the attending physician is satisfied that the puncture site may be sealed, is illustrated in FIG. 2. The device 101 may then be introduced over a guidewire 114, as illustrated in FIG. 2, and optionally through a support sheath 170. The needles 115 and sutures 112 mostly encased by flexible needle sheath 105, will be fully advanced into the artery or ventricle FA past the puncture site A. The handle 109N may then be partially withdrawn proximally to expose the needle lumens 119 (as shown in FIGS. 1, 4A and 4B).

The handle 109N will then be drawn proximally outward relative to the elongated member 113, causing the needles 115 to pass through the superficial wall of the artery/ventricle FA and into the needle lumens 119, as illustrated in FIGS. 2 and 4B. The handle 109N may continue to be drawn proximally (i.e., outward from the patient) in order to continue to pull the needle shaft 111 through the elongated member 113. Such movement of the needle shaft 111, in turn, continues to draw the needles 115 outward through the lumens 125 of the elongated member 113 until the tips of the needles are exposed.

As mentioned above, the needles 115 are drawn from out of needle lumens 125 and through any intervening tissue. The tissue may be thick and fibrous, as is the case when the tissue suturing device is inserted transapically into the heart. The device's elongated subsection 107 provides sufficient rigidity and stiffness for insertion through and placement in the thick and fibrous tissue. It is across this elongated subsection 107 and through this tissue that the needles 115 are withdrawn. In some cases, the needles 115 may deflect or drift while traveling through this tissue. Upon reaching the outer surface of the tissue, the needles may be guided into the semicircular openings 160 of the barrel portion 108. The needles will thus carry their attached sutures 112 through the tissue, across the elongated subsection 107, and through the barrel portion 108. The sutures can then be grasped by the user and drawn out until the sutures are available to the user. The elongated member 113 may then be withdrawn from the support sheath 170, leaving a portion of the needle sheath 105 still in the puncture site A to maintain hemostasis. The suture can then be tied and the knot pushed back down to the puncture site A. The knot will then only be tightened when the needle sheath is finally withdrawn from the puncture site A.

Figure 7:
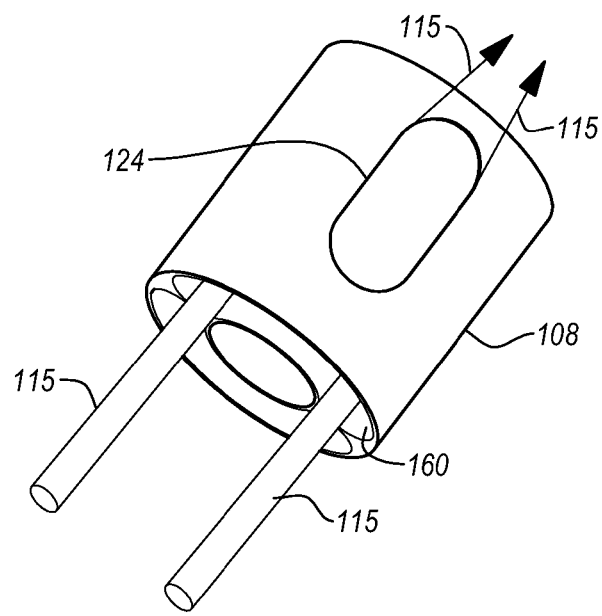
FIG. 7 illustrates a barrel comprising semi-circular openings on the distal end configured to draw the needles toward a narrow exit hole on the proximal end of the barrel.

It can be seen that the guide tip 123 deflects the needles radially outward so that the pattern of four needles engages the arterial or ventrical wall in an approximately square pattern. These needles are then captured by the barrel portion 108. As shown in FIG. 7, the barrel portion captures the needles 115 traveling toward the handle 109 (FIG. 1). The needles 115 enter the distal end of the barrel portion 108 through one of two semi-circular openings 160 (in some cases, there may be more or fewer openings, and the openings may be in shapes other than semi-circles). The outer surface at the proximal end of the barrel portion 108 includes a hole 124 connected to the semi-circular openings 160 through which the needles 115 are withdrawn. As such, the openings 160 direct the needles on a narrower trajectory toward the handle 109 of the suturing apparatus. The needles are drawn across the elongated subsection 107 in order to reach the barrel portion 108. The elongated subsection 107 may be a predefined length, and may be specifically designed for the tissue though which the elongated member 113 is to be inserted.

For instance, as mentioned above, when the suturing device 101 is transapically inserted into the left ventricle of the heart, the elongated subsection 107 may comprise a specific length (e.g. within the range of 1-5 cm) for that type and/or thickness of tissue. Other types of insertion may necessitate use of a longer or shorter elongated subsection 107. In some cases, the diameter of the barrel portion 108 may be proportional to the thickness of the tissue (i.e. the tissue gap). Thus, in cases where the tissue gap is longer (e.g. within the range of 4-5 cm) and the needles are more prone to drift, the barrel portion 108 may be larger. Conversely, in cases where the tissue gap is shorter (e.g. within the range of 1-2 cm) and the needles are less prone to drift, the barrel portion 108 may be smaller in diameter.

Figure 8:
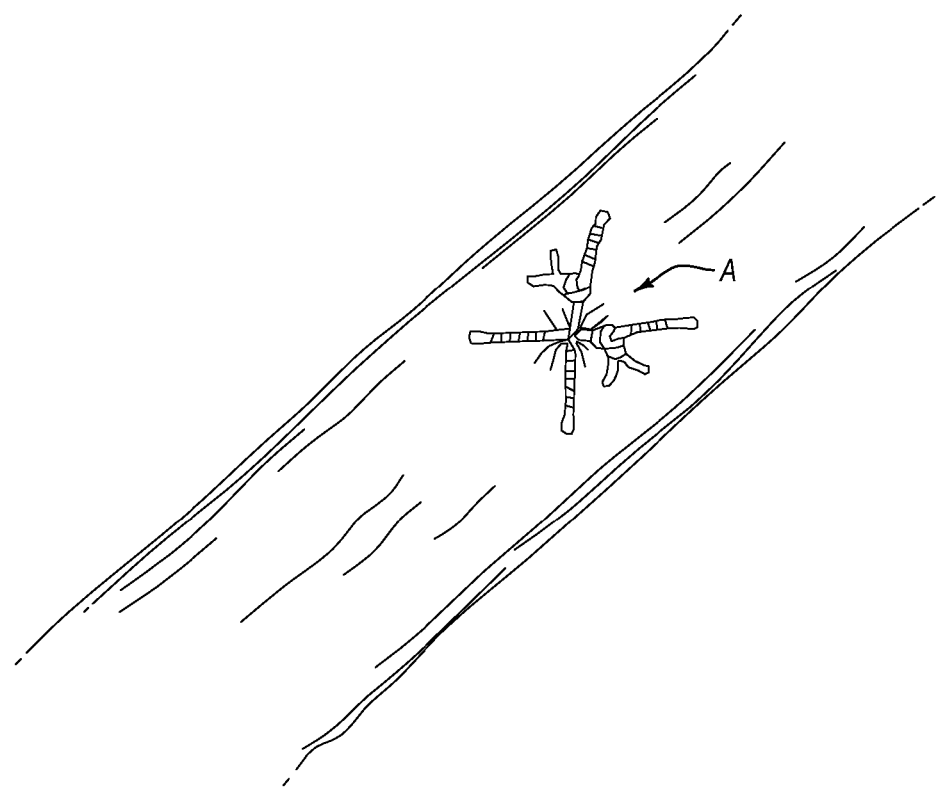
FIG. 8 illustrates the X-pattern of the tied suture applied by the suturing device.

In specific cases where the body lumen suturing device is inserted into the left ventricle of the heart transapically, and implemented to suture an opening in the left ventricle of the heart, the elongated portion 113 of the suturing apparatus 101 may be advanced through the body lumen opening so that the needle lumens 106 are entirely within the body lumen 150. The elongated member 113 of suturing apparatus 101 may be advanced in this manner until it is substantially aligned with the interior wall of the body lumen. One or more pledgets 116 stored at the proximal end of the needle lumens 106 in the elongated member 113 may be placed between the needle ends and the interior wall of the body lumen (as shown in FIG. 6C). The needles 115A/115B and attached sutures 112A/112B are withdrawn through holes 118 in the pledget(s) 116. As such, the pledgets remain in contact with the interior wall of the body lumen 150, protecting the interior wall from forces applied to the sutures. The handle 109 may then be actuated to withdraw the needles 115 carrying the sutures 112 along the needle lumens 106, through the interior wall of the body lumen 150, and out through the opening 124 of the barrel portion 108. After the sutures are tied and the knots advanced back through the support sheath 170, the resulting pattern of tied suture will appear as in FIG. 8 when viewed towards adventitial surface of the body.

Turning now to another embodiment, the tissue suturing apparatus 101 may further be designed to implement pledgets. As used herein, a pledget may refer to an absorbent pad or other cloth- or cotton-like material for absorbing bodily fluids. In some cases, the pledgets may be fabricated using biocompatible and/or absorbable materials, and may be used accordingly in different applications. For instance, pledgets may be placed interior to or exterior to a body lumen. Accordingly, a pledget may be placed inside an arterial wall, outside an arterial wall, or elsewhere in the body. In embodiments where pledgets are used in ventricles of the heart, the pledgets may protect the inner ventricle from cutting of the tissue by knot advancement, tying or by other causes. The pledgets may be stored at the end of the proximal end of the needle lumens 106. The sutures 112A/112B may be routed through holes the pledgets. These holes are large enough not to restrict suture travel. The pledgets may be held in place by crimp ring 104. These concepts will be explained below with regard to FIGS. 6A-6D.

FIG. 6A illustrates a zoomed-in view of the proximal end of the needle lumens 106, and the distal end of the elongated subsection 107. Needles 115A and 115B are shown still within the sheath 105 of the elongated member 113. Corresponding sutures 112A and 112B are attached to needles 115A and 115B. In some cases, the sutures may be of differing colors. For instance, suture 112A may be colored green, while suture 112B is colored white. The sutures may be drawn through a hole 118 in pledget 116. The pledget may be held in place by crimp ring 104 which extends around the elongated member 113.

As mentioned previously, the pledgets may be used both interior to and exterior to a vascular or arterial wall. Accordingly, FIG. 6B illustrates an embodiment where the pledget 116 is placed on the interior side of a body lumen (e.g. tissue 150). The sutures are threaded through the hole 118 in the pledget, and then through the tissue 150 as they are drawn toward the barrel portion 108 of the suturing apparatus. In this position, the pledget can alleviate bleeding in the vascular wall, and help to maintain hemostasis. Although shown with four needles 115 and two sutures, it should be noted that substantially any number of needles and/or sutures may be used in different scenarios. In some cases, it may be beneficial to have more or fewer needles and/or sutures. Accordingly, the suturing apparatus may be adapted (or remanufactured) to be used in these cases.

Thus, as shown in FIG. 6C, the sutures 112A/112B held by the needles 115 are threaded through the pledget 116, which is located between the sutures and the interior wall of the body lumen 150. In some cases, as shown in FIG. 6D, a second, different pledget may be placed in addition to (or as an alternative to) the pledget placed on the interior side of the body lumen (pledget 116B). Pledget 116A may be placed on the outside of the body lumen, and may function to alleviate bleeding on the outer part of the vascular wall. The exterior pledget (116A) may, like the interior pledget 116B, be threaded with sutures 112A and 112B. These sutures may be drawn through the pledget(s) and out through the puncture site (PS). Thus, in FIG. 6D, the sutures 112A/112B held by the needles 115 are threaded through the interior pledget 116B within the body lumen. The sutures 112A/112B are also threaded through the exterior pledget 116A which is exterior to the body lumen 150, such that the exterior pledget 116A is located between the exterior wall of the body lumen and the barrel portion 108 of the apparatus 101. The pledgets are stored at the proximal end 113P of the needle lumens 106 in the elongated member 113, and are held in place by a crimp ring 104 configured to hold the pledgets in place at the proximal end of the needle lumens 106 in the elongated member until they are withdrawn along with the sutures and the needles toward the barrel portion 108.

A pledget 116 includes slits in various locations. The slits may be placed on the outer edge of the pledget in order to allow a suture to be slid into place (as opposed to being threaded through a hole in the pledget). The pledget may have two slits on opposite sides. Each slit may have two sutures through it. Substantially any number of sutures and/or slits may be used. The sutures may be slid through the slits and wrapped underneath the pledget. The ends of the sutures 112A and 112B may come out of the top surface of the pledget. The pledget slits may be sewn or otherwise fastened shut, resulting in sewn edges. The edges may be sewn after the sutures have been slid into place. The slits thus allow the sutures to be slid into place on the pledget, while the sewn edges prevent the sutures from coming out of place.

These slits and sewn edges may be configured in different arrangements. A pledget 116 may include crossing sutures 112A and 112B. The sutures may be slid into place using the respective slits. The sutures may extend out of the slits toward the user and/or toward the tissue suturing device. The sutures may be held in place within the slits with the sewn edges. As with the pledgets described above, the pledgets can be held in place in the tissue suturing device 101 using crimp ring 104. Or, alternatively, the pledgets can be held in place by the sutures themselves. For example, if the sutures are crossed behind the suture, the pledget may be drawn up next to the tissue suturing device with the sutures holding the pledget in place. The sutures may be slid into place through slits, and may be aligned next to each other vertically. The top ends of the sutures 112A and 112B are then available for the user or device.

Accordingly, methods, systems and apparatuses are provided for suturing body lumens. A predefined tissue gap may be implemented to provide mechanisms for inserting the suturing device transapically into the left ventricle of the heart. Moreover, pledgets may be positioned within the suturing device for implementation on the exterior and interior walls of the body lumen. The placement of these pledgets may reduce blood loss and may assist in maintaining hemostasis.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. An apparatus for suturing a body lumen, the apparatus comprising:
   a flexible elongated member having a proximal end, a distal end, and a plurality of needle lumens extending from the proximal end toward the distal end, wherein the flexible elongated member comprises an elongated subsection spanning from the end of the needle lumens in the elongated member to a barrel portion comprising corresponding needle lumens on the proximal end of the elongated member, the elongated subsection providing sufficient space between the needles and the barrel portion to allow transapical insertion of the elongated member, the barrel portion comprising an outer surface and a distal surface extending transversely to a longitudinal axis of the flexible elongated member, the distal surface including one or more semi-circular openings;
   a plurality of needles disposed within and advanceable from the plurality of needle lumens in the flexible elongated member across the elongated subsection, through the one or more semi-circular openings, to one or more corresponding needle lumens in the barrel portion; and
   a handle disposed at the proximal end of the elongated member, the handle being operable to retract one or more of the plurality of needles through the needle lumens of the elongated member across the elongated subsection toward the handle at the proximal end, the barrel portion including a barrel opening through the outer surface of the barrel portion connected to the semi-circular openings through which the needles are withdrawn.

2. The apparatus of claim 1, further comprising a first pledget.

3. The apparatus of claim 2, wherein the first pledget is located within the body lumen.

4. The apparatus of claim 3, wherein sutures held by the needles are threaded through the first pledget, wherein the first pledget is located between the suture and the interior wall of the body lumen.

5. The apparatus of claim 4, further comprising a second pledget located exterior to the body lumen.

6. The apparatus of claim 5, wherein sutures held by the needles are threaded through the first pledget within the body lumen, wherein the first pledget is located between the suture and the interior wall of the body lumen, and wherein the sutures are further threaded through the second pledget exterior to the body lumen, wherein the second pledget is located between the exterior wall of the body lumen and the barrel portion of the apparatus.

7. The apparatus of claim 4, wherein the pledgets are stored at the proximal end of the needle lumens in the elongated member.

8. The apparatus of claim 7, wherein the elongated member comprises a crimp ring configured to hold the pledgets in place at the proximal end of the needle lumens in the elongated member.

9. The apparatus of claim 4, wherein at least one of the pledgets includes slits on one or more outer edges of the pledget through which the sutures are each pulled into appropriate positions on the pledget.

10. The apparatus of claim 9, wherein one or more of the pledget slits are sewn together on the outer edge of the slit.

11. The apparatus of claim 10, wherein a sewn edge of the pledget slit prevents the sutures from sliding out of the pledget.

12. The apparatus of claim 1, wherein the elongated subsection spans a predefined tissue gap length.

13. The apparatus of claim 7, wherein a diameter of the barrel portion is proportional to the tissue gap.

14. A method for suturing an opening in a body lumen, the body lumen being accessed in a transapical manner, the method comprising:
   providing a body lumen suturing device, the body lumen suturing device comprising:
      a flexible elongated member having a proximal end, a distal end, and a plurality of needle lumens extending from the proximal end toward the distal end, wherein the flexible elongated member comprises an elongated subsection spanning from the end of the needle lumens in the elongated member to a barrel portion comprising corresponding needle lumens on the proximal end of the elongated member, the elongated subsection providing sufficient space between the needles and the barrel portion to allow transapical insertion of the elongated member, the barrel portion comprising a distal surface extending transversely to a longitudinal axis of the flexible elongated member and an outer surface, the distal surface including one or more semi-circular openings, the barrel portion including a barrel opening through the outer surface of the barrel portion connected to the semi-circular openings, a plurality of needles disposed within and advanceable from the plurality of needle lumens in the flexible elongated member across the elongated subsection, through the one or more semi-circular openings, to one or more corresponding needle lumens in the barrel portion; and a handle disposed at the proximal end of the elongated member, the handle being operable to retract one or more of the plurality of needles through the needle lumens of the elongated member across the elongated subsection toward the handle at the proximal end;

advancing the elongated member through the body lumen opening such that the needle lumens are entirely within the body lumen and the elongated subsection is substantially aligned with the interior wall of the body lumen; and actuating the handle to withdraw the needles carrying the sutures along the needle lumens of the elongate member, through the interior wall of the body lumen, across the elongated subsection, enter the one or more semi-circular openings and further through the barrel opening, and out through the corresponding needle lumens in the barrel portion.

15. The method of claim 14, wherein the body lumen suturing device is inserted into the left ventricle of the heart transapically, and implemented to suture an opening in the left ventricle of the heart.

16. The method of claim 15, wherein one or more pledgets stored at the proximal end of the needle lumens in the elongated member are placed between the needle ends and the interior wall of the body lumen.

17. The method of claim 16, wherein the needles and attached sutures are withdrawn through holes in the pledgets, such that the pledgets remain in contact with the interior wall of the body lumen, protecting the interior wall from forces applied to the sutures.

18. A body lumen suturing device comprising the following:

a flexible elongated member having a proximal end, a distal end, and a plurality of needle lumens extending from the proximal end toward the distal end, wherein the flexible elongated member comprises an elongated subsection spanning from the end of the needle lumens in the elongated member to a barrel portion comprising corresponding needle lumens on the proximal end of the elongated member, the elongated subsection providing sufficient space between the needles and the barrel portion to allow transapical insertion of the elongated member, the barrel portion comprising an outer surface and a distal surface extending transversely to a longitudinal axis of the flexible elongated member, the distal surface including one or more semi-circular openings, wherein the elongated member comprises a crimp ring configured to hold pledgets in place at the proximal end of the needle lumens in the elongated member;

a plurality of needles disposed within and advanceable from the plurality of needle lumens in the flexible elongated member across the elongated subsection, through the one or more semi-circular openings, to one or more corresponding needle lumens in the barrel portion;

one or more pledgets stored at the proximal end of the needle lumens in the elongated member, wherein the pledgets include one or more holes through which the sutures are pulled; and a handle disposed at the proximal end of the elongated member, the handle being operable to retract one or more of the plurality of needles through the needle lumens of the elongated member across the elongated subsection toward the handle at the proximal end, the barrel portion including a barrel opening through the outer surface of the barrel portion connected to the semi-circular openings through which the needles are withdrawn.

* * * * *